(12) United States Patent
Baima et al.

(10) Patent No.: US 12,285,479 B2
(45) Date of Patent: Apr. 29, 2025

(54) ANTI-CORONAVIRUS VACCINES

(71) Applicant: Zoetis Services LLC, Parsippany, NJ (US)

(72) Inventors: Eric Todd Baima, Kalamazoo, MI (US); Yulia Burakova, Byron Center, MI (US); Paul Joseph Dominowski, Kalamazoo, MI (US); Steven Alan Dunham, Kalamazoo, MI (US); Nicole Lynn Hainer, Kalamazoo, MI (US); John Morgan Hardham, Kalamazoo, MI (US); Mahesh Kumar, Portage, MI (US); Jason John Millership, Portage, MI (US); Duncan M. Mwangi, Portage, MI (US); Sharath K. Rai, Portage, MI (US); Sharon Marie Wappel, Kalamazoo, MI (US); Dennis Lee Foss, Mattawan, MI (US)

(73) Assignee: Zoetis Services LLC, Parsippany, NJ (US)

( * ) Notice: Subject to any disclaimer, the term of this patent is extended or adjusted under 35 U.S.C. 154(b) by 543 days.

(21) Appl. No.: 17/389,724

(22) Filed: Jul. 30, 2021

(65) Prior Publication Data

US 2022/0047696 A1 Feb. 17, 2022

Related U.S. Application Data

(60) Provisional application No. 63/145,045, filed on Feb. 3, 2021, provisional application No. 63/088,708, filed on Oct. 7, 2020, provisional application No. 63/064,225, filed on Aug. 11, 2020.

(51) Int. Cl.
*A61K 39/215* (2006.01)
*A61K 39/00* (2006.01)
*A61P 31/14* (2006.01)

(52) U.S. Cl.
CPC ............ *A61K 39/215* (2013.01); *A61P 31/14* (2018.01); *A61K 2039/525* (2013.01); *A61K 2039/545* (2013.01); *A61K 2039/552* (2013.01); *A61K 2039/55511* (2013.01); *A61K 2039/55561* (2013.01); *A61K 2039/55577* (2013.01); *A61K 2039/55588* (2013.01)

(58) Field of Classification Search
CPC ............ A61K 39/215; A61K 2039/525; A61K 2039/545; A61K 2039/552; A61K 2039/55511; A61K 2039/55561; A61K 2039/55577; A61K 2039/55588; A61P 31/14
See application file for complete search history.

(56) References Cited

U.S. PATENT DOCUMENTS

| | | | | |
|---|---|---|---|---|
| 7,122,191 | B2 * | 10/2006 | Dominowski | A61P 33/00 424/283.1 |
| 9,662,385 | B2 | 5/2017 | Dominowski et al. | |
| 10,953,080 | B2 * | 3/2021 | Dominowski | A61K 39/05 |
| 11,192,940 | B2 * | 12/2021 | Walker | C07K 16/1002 |
| 11,701,415 | B2 * | 7/2023 | Dominowski | A61P 37/08 424/203.1 |
| 11,896,666 | B2 * | 2/2024 | Dominowski | A61K 39/12 |
| 2005/0220814 | A1 | 10/2005 | Dominowski et al. | |
| 2013/0084306 | A1 * | 4/2013 | Davis | A61K 39/099 424/193.1 |
| 2022/0050102 | A1 * | 2/2022 | Lizer | G01N 33/54388 |
| 2024/0000913 | A1 * | 1/2024 | Dominowski | A61K 39/39 |

FOREIGN PATENT DOCUMENTS

| | | | | |
|---|---|---|---|---|
| WO | WO 2004/067031 A1 | 8/2004 | | |
| WO | WO-2014186291 A1 * | 11/2014 | | A61K 39/008 |
| WO | WO-2015042449 A2 * | 3/2015 | | A61K 39/0003 |
| WO | WO 2017/015252 A1 | 1/2017 | | |
| WO | WO-2021188969 A2 * | 9/2021 | | A61K 39/12 |
| WO | WO-2021243248 A2 * | 12/2021 | | A61K 39/215 |
| WO | WO-2021263131 A1 * | 12/2021 | | A61K 31/7088 |

OTHER PUBLICATIONS

Wrobel, A. G., Benton, D. J., Xu, P., Roustan, C., Martin, S. R., Rosenthal, P. B., Skehel, J. J., & Gamblin, S. J. (2020). SARS-CoV-2 and bat RaTG13 spike glycoprotein structures inform on virus evolution and furin-cleavage effects. Nature structural & molecular biology, 27(8), 763-767. (Year: 2020).*

Wrobel et al. PDB: 6ZGE_A. Direct Submission. Submitted Jun. 18, 2020. (Year: 2020).*

* cited by examiner

*Primary Examiner* — Janet L Andres
*Assistant Examiner* — Carey Alexander Stuart
(74) *Attorney, Agent, or Firm* — Vyacheslav Vasilyev

(57) ABSTRACT

The invention provides stable coronavirus spike proteins. Immunogenic compositions comprising same and the methods of using these immunogenic compositions are also provided.

13 Claims, No Drawings

Specification includes a Sequence Listing.

SEQUENCE LISTING

```
<160> NUMBER OF SEQ ID NOS: 17

<210> SEQ ID NO 1
<211> LENGTH: 23
<212> TYPE: DNA
<213> ORGANISM: artificial
<220> FEATURE:
<223> OTHER INFORMATION: immunostimulatory oligonucleotide
<220> FEATURE:
<221> NAME/KEY: misc_structure
<222> LOCATION: (1)..(1)
<223> OTHER INFORMATION: phosphorothioate bond
<220> FEATURE:
<221> NAME/KEY: misc_structure
<222> LOCATION: (3)..(4)
<223> OTHER INFORMATION: phosphorothioate bond
<220> FEATURE:
<221> NAME/KEY: misc_structure
<222> LOCATION: (6)..(7)
<223> OTHER INFORMATION: phosphorothioate bond
<220> FEATURE:
<221> NAME/KEY: misc_structure
<222> LOCATION: (9)..(11)
<223> OTHER INFORMATION: phosphorothioate bond
<220> FEATURE:
<221> NAME/KEY: misc_structure
<222> LOCATION: (13)..(16)
```

```
<223> OTHER INFORMATION: phosphorothioate bond
<220> FEATURE:
<221> NAME/KEY: misc_structure
<222> LOCATION: (18)..(22)
<223> OTHER INFORMATION: phosphorothioate bond

<400> SEQUENCE: 1
tcgtcgacga tcggcgcgcg ccg                                                  23

<210> SEQ ID NO 2
<211> LENGTH: 23
<212> TYPE: DNA
<213> ORGANISM: artificial
<220> FEATURE:
<223> OTHER INFORMATION: immunostimulatory oligonucleotide
<220> FEATURE:
<221> NAME/KEY: misc_feature
<222> LOCATION: (1)..(1)
<223> OTHER INFORMATION: phosphorotioate bond
<220> FEATURE:
<221> NAME/KEY: misc_feature
<222> LOCATION: (3)..(22)
<223> OTHER INFORMATION: phosphorotioate bond

<400> SEQUENCE: 2
tcgacgtcga tcggcgcgcg ccg                                                  23

<210> SEQ ID NO 3
<211> LENGTH: 24
<212> TYPE: DNA
<213> ORGANISM: artificial
<220> FEATURE:
<223> OTHER INFORMATION: immunostimulatory oligonucleotide
<220> FEATURE:
<221> NAME/KEY: misc_feature
<222> LOCATION: (1)..(23)
<223> OTHER INFORMATION: phosphorotioate bonds

<400> SEQUENCE: 3
tcgacgtcga tcggcgcgcg ccgt                                                 24

<210> SEQ ID NO 4
<211> LENGTH: 23
<212> TYPE: DNA
<213> ORGANISM: artificial
<220> FEATURE:
<223> OTHER INFORMATION: immunostimulatory oligonucleotide
<220> FEATURE:
<221> NAME/KEY: modified_base
<222> LOCATION: (1)..(1)
<223> OTHER INFORMATION: iodouridine
<220> FEATURE:
<221> NAME/KEY: misc_feature
<222> LOCATION: (1)..(1)
<223> OTHER INFORMATION: phosphorotioate bond
<220> FEATURE:
<221> NAME/KEY: misc_feature
<222> LOCATION: (3)..(22)
<223> OTHER INFORMATION: phosphorotioate bond

<400> SEQUENCE: 4
ncgacgtcga tcggcgcgcg ccg                                                  23

<210> SEQ ID NO 5
<211> LENGTH: 24
<212> TYPE: DNA
<213> ORGANISM: artificial
<220> FEATURE:
<223> OTHER INFORMATION: immunostimulatory oligonucleotide
<220> FEATURE:
<221> NAME/KEY: modified_base
```

```
<222> LOCATION: (1)..(1)
<223> OTHER INFORMATION: iodouridine
<220> FEATURE:
<221> NAME/KEY: misc_feature
<222> LOCATION: (1)..(1)
<223> OTHER INFORMATION: phosphorotioate bond
<220> FEATURE:
<221> NAME/KEY: misc_feature
<222> LOCATION: (1)..(1)
<223> OTHER INFORMATION: phosphorotioate bond

<400> SEQUENCE: 5
ncgacgtcga tcggcgcgcg ccgt                                          24

<210> SEQ ID NO 6
<211> LENGTH: 24
<212> TYPE: DNA
<213> ORGANISM: artificial
<220> FEATURE:
<223> OTHER INFORMATION: immunostimulatory oligonucleotide
<220> FEATURE:
<221> NAME/KEY: modified_base
<222> LOCATION: (1)..(1)
<223> OTHER INFORMATION: iodouridine
<220> FEATURE:
<221> NAME/KEY: misc_feature
<222> LOCATION: (1)..(23)
<223> OTHER INFORMATION: phosphorotioate bonds

<400> SEQUENCE: 6
ncgacgtcga tcggcgcgcg ccgt                                          24

<210> SEQ ID NO 7
<211> LENGTH: 23
<212> TYPE: DNA
<213> ORGANISM: artificial
<220> FEATURE:
<223> OTHER INFORMATION: immunostimulatory oligonucleotide
<220> FEATURE:
<221> NAME/KEY: modified_base
<222> LOCATION: (1)..(1)
<223> OTHER INFORMATION: Ethyl-uridine
<220> FEATURE:
<221> NAME/KEY: misc_feature
<222> LOCATION: (1)..(1)
<223> OTHER INFORMATION: phosphorotioate bond
<220> FEATURE:
<221> NAME/KEY: misc_feature
<222> LOCATION: (3)..(22)
<223> OTHER INFORMATION: phosphorotioate bond

<400> SEQUENCE: 7
ncgacgtcga tcggcgcgcg ccg                                           23

<210> SEQ ID NO 8
<211> LENGTH: 24
<212> TYPE: DNA
<213> ORGANISM: artificial
<220> FEATURE:
<223> OTHER INFORMATION: immunostimulatory oligonucleotide
<220> FEATURE:
<221> NAME/KEY: modified_base
<222> LOCATION: (1)..(1)
<223> OTHER INFORMATION: iodouridine
<220> FEATURE:
<221> NAME/KEY: misc_feature
<222> LOCATION: (1)..(1)
<223> OTHER INFORMATION: phosphorotioate bond
<220> FEATURE:
<221> NAME/KEY: misc_feature
<222> LOCATION: (3)..(23)
<223> OTHER INFORMATION: phosphorotioate bond
```

-continued

```
<400> SEQUENCE: 8
ncgtcgacga tcggcggccg ccgt                                        24

<210> SEQ ID NO 9
<211> LENGTH: 24
<212> TYPE: DNA
<213> ORGANISM: artificial
<220> FEATURE:
<223> OTHER INFORMATION: immunostimulatory oligonucleotide
<220> FEATURE:
<221> NAME/KEY: modified_base
<222> LOCATION: (1)..(1)
<223> OTHER INFORMATION: iodouridine
<220> FEATURE:
<221> NAME/KEY: misc_feature
<222> LOCATION: (1)..(23)
<223> OTHER INFORMATION: phosphorotioate bonds

<400> SEQUENCE: 9
ncgtcgacga tcggcggccg ccgt                                        24

<210> SEQ ID NO 10
<211> LENGTH: 23
<212> TYPE: DNA
<213> ORGANISM: artificial
<220> FEATURE:
<223> OTHER INFORMATION: immunostimulatory oligonucleotide
<220> FEATURE:
<221> NAME/KEY: misc_feature
<222> LOCATION: (1)..(1)
<223> OTHER INFORMATION: phosphorotioate bond
<220> FEATURE:
<221> NAME/KEY: misc_feature
<222> LOCATION: (3)..(4)
<223> OTHER INFORMATION: phosphorotioate bonds
<220> FEATURE:
<221> NAME/KEY: misc_feature
<222> LOCATION: (6)..(7)
<223> OTHER INFORMATION: phosphorotioate bonds
<220> FEATURE:
<221> NAME/KEY: misc_feature
<222> LOCATION: (9)..(11)
<223> OTHER INFORMATION: phosphorotioate bonds
<220> FEATURE:
<221> NAME/KEY: misc_feature
<222> LOCATION: (13)..(16)
<223> OTHER INFORMATION: phosphorotioate bonds
<220> FEATURE:
<221> NAME/KEY: misc_feature
<222> LOCATION: (18)..(22)
<223> OTHER INFORMATION: phosphorotioate bonds

<400> SEQUENCE: 10
tcgtcgacga tcggcgcgcg ccg                                         23

<210> SEQ ID NO 11
<211> LENGTH: 1273
<212> TYPE: PRT
<213> ORGANISM: SARS-CoV2
<220> FEATURE:
<221> NAME/KEY: MISC_FEATURE
<223> OTHER INFORMATION: Spike protein

<400> SEQUENCE: 11

Met Phe Val Phe Leu Val Leu Leu Pro Leu Val Ser Ser Gln Cys Val
  1               5                  10                  15

Asn Leu Thr Thr Arg Thr Gln Leu Pro Pro Ala Tyr Thr Asn Ser Phe
             20                  25                  30

Thr Arg Gly Val Tyr Tyr Pro Asp Lys Val Phe Arg Ser Ser Val Leu
         35                  40                  45
```

His Ser Thr Gln Asp Leu Phe Leu Pro Phe Phe Ser Asn Val Thr Trp
 50                  55                  60

Phe His Ala Ile His Val Ser Gly Thr Asn Gly Thr Lys Arg Phe Asp
 65              70                  75                  80

Asn Pro Val Leu Pro Phe Asn Asp Gly Val Tyr Phe Ala Ser Thr Glu
                 85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

-continued

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
            485                 490                 495

Phe Gln Pro Thr Asn Gly Val Gly Tyr Gln Pro Tyr Arg Val Val Val
        500                 505                 510

Leu Ser Phe Glu Leu Leu His Ala Pro Ala Thr Val Cys Gly Pro Lys
    515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
        580                 585                 590

Gly Gly Val Ser Val Ile Thr Pro Gly Thr Asn Thr Ser Asn Gln Val
    595                 600                 605

Ala Val Leu Tyr Gln Asp Val Asn Cys Thr Glu Val Pro Val Ala Ile
610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
        660                 665                 670

Ser Tyr Gln Thr Gln Thr Asn Ser Pro Arg Arg Ala Arg Ser Val Ala
    675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
        740                 745                 750

Leu Leu Gln Tyr Gly Ser Phe Cys Thr Gln Leu Asn Arg Ala Leu Thr
    755                 760                 765

Gly Ile Ala Val Glu Gln Asp Lys Asn Thr Gln Glu Val Phe Ala Gln
770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
        820                 825                 830

Phe Ile Lys Gln Tyr Gly Asp Cys Leu Gly Asp Ile Ala Ala Arg Asp
    835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile

```
                885                 890                 895
Pro Phe Ala Met Gln Met Ala Tyr Arg Phe Asn Gly Ile Gly Val Thr
                    900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn
    1010                1015                1020

Leu Ala Ala Thr Lys Met Ser Glu Cys Val Leu Gly Gln Ser Lys
    1025                1030                1035

Arg Val Asp Phe Cys Gly Lys Gly Tyr His Leu Met Ser Phe Pro
    1040                1045                1050

Gln Ser Ala Pro His Gly Val Val Phe Leu His Val Thr Tyr Val
    1055                1060                1065

Pro Ala Gln Glu Lys Asn Phe Thr Thr Ala Pro Ala Ile Cys His
    1070                1075                1080

Asp Gly Lys Ala His Phe Pro Arg Glu Gly Val Phe Val Ser Asn
    1085                1090                1095

Gly Thr His Trp Phe Val Thr Gln Arg Asn Phe Tyr Glu Pro Gln
    1100                1105                1110

Ile Ile Thr Thr Asp Asn Thr Phe Val Ser Gly Asn Cys Asp Val
    1115                1120                1125

Val Ile Gly Ile Val Asn Asn Thr Val Tyr Asp Pro Leu Gln Pro
    1130                1135                1140

Glu Leu Asp Ser Phe Lys Glu Glu Leu Asp Lys Tyr Phe Lys Asn
    1145                1150                1155

His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 12
```

<211> LENGTH: 27
<212> TYPE: PRT
<213> ORGANISM: artificial
<220> FEATURE:
<223> OTHER INFORMATION: fibriton foldon

<400> SEQUENCE: 12

Gly Tyr Ile Pro Glu Ala Pro Arg Gly Asp Gln Ala Tyr Val Arg Lys
1               5                   10                  15

Asp Gly Glu Trp Val Leu Leu Ser Thr Phe Leu
            20                  25

<210> SEQ ID NO 13
<211> LENGTH: 1195
<212> TYPE: PRT
<213> ORGANISM: Artificial
<220> FEATURE:
<223> OTHER INFORMATION: SARS_CoV Spike protien without signal peptide

<400> SEQUENCE: 13

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
65                  70                  75                  80

Ser Thr Glu Lys Ser Asn Ile Ile Arg Gly Trp Ile Phe Gly Thr Thr
                85                  90                  95

Leu Asp Ser Lys Thr Gln Ser Leu Leu Ile Val Asn Asn Ala Thr Asn
            100                 105                 110

Val Val Ile Lys Val Cys Glu Phe Gln Phe Cys Asn Asp Pro Phe Leu
        115                 120                 125

Gly Val Tyr Tyr His Lys Asn Asn Lys Ser Trp Met Glu Ser Glu Phe
    130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                165                 170                 175

Arg Glu Phe Val Phe Lys Asn Ile Asp Gly Tyr Phe Lys Ile Tyr Ser
            180                 185                 190

Lys His Thr Pro Ile Asn Leu Val Arg Asp Leu Pro Gln Gly Phe Ser
        195                 200                 205

Ala Leu Glu Pro Leu Val Asp Leu Pro Ile Gly Ile Asn Ile Thr Arg
    210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                245                 250                 255

Leu Gln Pro Arg Thr Phe Leu Leu Lys Tyr Asn Glu Asn Gly Thr Ile
            260                 265                 270

Thr Asp Ala Val Asp Cys Ala Leu Asp Pro Leu Ser Glu Thr Lys Cys
        275                 280                 285

Thr Leu Lys Ser Phe Thr Val Glu Lys Gly Ile Tyr Gln Thr Ser Asn

```
            290                 295                 300
Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                    325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
            355                 360                 365

Val Ser Pro Thr Lys Leu Asn Asp Leu Cys Phe Thr Asn Val Tyr Ala
        370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                    405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
            435                 440                 445

Lys Pro Phe Glu Arg Asp Ile Ser Thr Glu Ile Tyr Gln Ala Gly Ser
        450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                    485                 490                 495

Val Val Val Leu Ser Phe Glu Leu Leu His Ala Pro Ala Thr Val Cys
                500                 505                 510

Gly Pro Lys Lys Ser Thr Asn Leu Val Lys Asn Lys Cys Val Asn Phe
            515                 520                 525

Asn Phe Asn Gly Leu Thr Gly Thr Gly Val Leu Thr Glu Ser Asn Lys
        530                 535                 540

Lys Phe Leu Pro Phe Gln Gln Phe Gly Arg Asp Ile Ala Asp Thr Thr
545                 550                 555                 560

Asp Ala Val Arg Asp Pro Gln Thr Leu Glu Ile Leu Asp Ile Thr Pro
                    565                 570                 575

Cys Ser Phe Gly Gly Val Ser Val Ile Thr Pro Gly Thr Asn Thr Ser
                580                 585                 590

Asn Gln Val Ala Val Leu Tyr Gln Asp Val Asn Cys Thr Glu Val Pro
            595                 600                 605

Val Ala Ile His Ala Asp Gln Leu Thr Pro Thr Trp Arg Val Tyr Ser
        610                 615                 620

Thr Gly Ser Asn Val Phe Gln Thr Arg Ala Gly Cys Leu Ile Gly Ala
625                 630                 635                 640

Glu His Val Asn Asn Ser Tyr Glu Cys Asp Ile Pro Ile Gly Ala Gly
                    645                 650                 655

Ile Cys Ala Ser Tyr Gln Thr Gln Thr Asn Ser Pro Gly Ser Ala Ser
                660                 665                 670

Ser Val Ala Ser Gln Ser Ile Ile Ala Tyr Thr Met Ser Leu Gly Ala
            675                 680                 685

Glu Asn Ser Val Ala Tyr Ser Asn Asn Ser Ile Ala Ile Pro Thr Asn
        690                 695                 700

Phe Thr Ile Ser Val Thr Thr Glu Ile Leu Pro Val Ser Met Thr Lys
705                 710                 715                 720
```

-continued

```
Thr Ser Val Asp Cys Thr Met Tyr Ile Cys Gly Asp Ser Thr Glu Cys
                725                 730                 735

Ser Asn Leu Leu Leu Gln Tyr Gly Ser Phe Cys Thr Gln Leu Asn Arg
        740                 745                 750

Ala Leu Thr Gly Ile Ala Val Glu Gln Asp Lys Asn Thr Gln Glu Val
            755                 760                 765

Phe Ala Gln Val Lys Gln Ile Tyr Lys Thr Pro Pro Ile Lys Asp Phe
        770                 775                 780

Gly Gly Phe Asn Phe Ser Gln Ile Leu Pro Asp Pro Ser Lys Pro Ser
785                 790                 795                 800

Lys Arg Ser Phe Ile Glu Asp Leu Leu Phe Asn Lys Val Thr Leu Ala
                805                 810                 815

Asp Ala Gly Phe Ile Lys Gln Tyr Gly Asp Cys Leu Gly Asp Ile Ala
                820                 825                 830

Ala Arg Asp Leu Ile Cys Ala Gln Lys Phe Asn Gly Leu Thr Val Leu
                835                 840                 845

Pro Pro Leu Leu Thr Asp Glu Met Ile Ala Gln Tyr Thr Ser Ala Leu
        850                 855                 860

Leu Ala Gly Thr Ile Thr Ser Gly Trp Thr Phe Gly Ala Gly Ala Ala
865                 870                 875                 880

Leu Gln Ile Pro Phe Ala Met Gln Met Ala Tyr Arg Phe Asn Gly Ile
                885                 890                 895

Gly Val Thr Gln Asn Val Leu Tyr Glu Asn Gln Lys Leu Ile Ala Asn
                900                 905                 910

Gln Phe Asn Ser Ala Ile Gly Lys Ile Gln Asp Ser Leu Ser Ser Thr
        915                 920                 925

Ala Ser Ala Leu Gly Lys Leu Gln Asp Val Val Asn Gln Asn Ala Gln
        930                 935                 940

Ala Leu Asn Thr Leu Val Lys Gln Leu Ser Ser Asn Phe Gly Ala Ile
945                 950                 955                 960

Ser Ser Val Leu Asn Asp Ile Leu Ser Arg Leu Asp Pro Pro Glu Ala
                965                 970                 975

Glu Val Gln Ile Asp Arg Leu Ile Thr Gly Arg Leu Gln Ser Leu Gln
                980                 985                 990

Thr Tyr Val Thr Gln Gln Leu Ile Arg Ala Ala Glu Ile Arg Ala Ser
        995                 1000                1005

Ala Asn Leu Ala Ala Thr Lys Met Ser Glu Cys Val Leu Gly Gln
1010                1015                1020

Ser Lys Arg Val Asp Phe Cys Gly Lys Gly Tyr His Leu Met Ser
1025                1030                1035

Phe Pro Gln Ser Ala Pro His Gly Val Val Phe Leu His Val Thr
1040                1045                1050

Tyr Val Pro Ala Gln Glu Lys Asn Phe Thr Thr Ala Pro Ala Ile
1055                1060                1065

Cys His Asp Gly Lys Ala His Phe Pro Arg Glu Gly Val Phe Val
1070                1075                1080

Ser Asn Gly Thr His Trp Phe Val Thr Gln Arg Asn Phe Tyr Glu
1085                1090                1095

Pro Gln Ile Ile Thr Thr Asp Asn Thr Phe Val Ser Gly Asn Cys
1100                1105                1110

Asp Val Val Ile Gly Ile Val Asn Asn Thr Val Tyr Asp Pro Leu
1115                1120                1125
```

-continued

```
Gln Pro  Glu Leu Asp Ser Phe  Lys Glu Glu Leu Asp  Lys Tyr Phe
    1130                 1135                 1140

Lys Asn  His Thr Ser Pro Asp  Val Asp Leu Gly Asp  Ile Ser Gly
    1145                 1150                 1155

Ile Asn  Ala Ser Val Val Asn  Ile Gln Lys Glu Ile  Asp Arg Leu
    1160                 1165                 1170

Asn Glu  Val Ala Lys Asn Leu  Asn Glu Ser Leu Ile  Asp Leu Gln
    1175                 1180                 1185

Glu Leu  Gly Lys Tyr Glu Gln
    1190                 1195

<210> SEQ ID NO 14
<211> LENGTH: 13
<212> TYPE: PRT
<213> ORGANISM: Artificial
<220> FEATURE:
<223> OTHER INFORMATION: Signal peptide

<400> SEQUENCE: 14

Met Phe Val Phe Leu Val Leu Leu Pro Leu Val Ser Ser
1               5                   10

<210> SEQ ID NO 15
<211> LENGTH: 6
<212> TYPE: PRT
<213> ORGANISM: Artificial
<220> FEATURE:
<223> OTHER INFORMATION: Furin Cleavage Site in Spike Protein of
      SARS_CoV2

<400> SEQUENCE: 15

Pro Arg Arg Ala Arg Ser
1               5

<210> SEQ ID NO 16
<211> LENGTH: 6
<212> TYPE: PRT
<213> ORGANISM: Artificial
<220> FEATURE:
<223> OTHER INFORMATION: mutated furin cleavage site of Spike protein of
      SARS-CoV2

<400> SEQUENCE: 16

Pro Gly Ser Ala Ser Ser
1               5

<210> SEQ ID NO 17
<211> LENGTH: 1229
<212> TYPE: PRT
<213> ORGANISM: Artificial
<220> FEATURE:
<223> OTHER INFORMATION: recombinant Spike protein of SARS-CoV2

<400> SEQUENCE: 17

Gln Cys Val Asn Leu Thr Thr Arg Thr Gln Leu Pro Pro Ala Tyr Thr
1               5                   10                  15

Asn Ser Phe Thr Arg Gly Val Tyr Tyr Pro Asp Lys Val Phe Arg Ser
            20                  25                  30

Ser Val Leu His Ser Thr Gln Asp Leu Phe Leu Pro Phe Phe Ser Asn
        35                  40                  45

Val Thr Trp Phe His Ala Ile His Val Ser Gly Thr Asn Gly Thr Lys
    50                  55                  60

Arg Phe Asp Asn Pro Val Leu Pro Phe Asn Asp Gly Val Tyr Phe Ala
```

```
                65                  70                  75                  80
Ser Thr Glu Lys Ser Asn Ile Ile Arg Gly Trp Ile Phe Gly Thr Thr
                    85                  90                  95

Leu Asp Ser Lys Thr Gln Ser Leu Leu Ile Val Asn Asn Ala Thr Asn
                100                 105                 110

Val Val Ile Lys Val Cys Glu Phe Gln Phe Cys Asn Asp Pro Phe Leu
                115                 120                 125

Gly Val Tyr Tyr His Lys Asn Asn Lys Ser Trp Met Glu Ser Glu Phe
            130                 135                 140

Arg Val Tyr Ser Ser Ala Asn Asn Cys Thr Phe Glu Tyr Val Ser Gln
145                 150                 155                 160

Pro Phe Leu Met Asp Leu Glu Gly Lys Gln Gly Asn Phe Lys Asn Leu
                    165                 170                 175

Arg Glu Phe Val Phe Lys Asn Ile Asp Gly Tyr Phe Lys Ile Tyr Ser
                180                 185                 190

Lys His Thr Pro Ile Asn Leu Val Arg Asp Leu Pro Gln Gly Phe Ser
                195                 200                 205

Ala Leu Glu Pro Leu Val Asp Leu Pro Ile Gly Ile Asn Ile Thr Arg
            210                 215                 220

Phe Gln Thr Leu Leu Ala Leu His Arg Ser Tyr Leu Thr Pro Gly Asp
225                 230                 235                 240

Ser Ser Ser Gly Trp Thr Ala Gly Ala Ala Ala Tyr Tyr Val Gly Tyr
                    245                 250                 255

Leu Gln Pro Arg Thr Phe Leu Leu Lys Tyr Asn Glu Asn Gly Thr Ile
                260                 265                 270

Thr Asp Ala Val Asp Cys Ala Leu Asp Pro Leu Ser Glu Thr Lys Cys
                275                 280                 285

Thr Leu Lys Ser Phe Thr Val Glu Lys Gly Ile Tyr Gln Thr Ser Asn
            290                 295                 300

Phe Arg Val Gln Pro Thr Glu Ser Ile Val Arg Phe Pro Asn Ile Thr
305                 310                 315                 320

Asn Leu Cys Pro Phe Gly Glu Val Phe Asn Ala Thr Arg Phe Ala Ser
                    325                 330                 335

Val Tyr Ala Trp Asn Arg Lys Arg Ile Ser Asn Cys Val Ala Asp Tyr
                340                 345                 350

Ser Val Leu Tyr Asn Ser Ala Ser Phe Ser Thr Phe Lys Cys Tyr Gly
                355                 360                 365

Val Ser Pro Thr Lys Leu Asn Asp Leu Cys Phe Thr Asn Val Tyr Ala
            370                 375                 380

Asp Ser Phe Val Ile Arg Gly Asp Glu Val Arg Gln Ile Ala Pro Gly
385                 390                 395                 400

Gln Thr Gly Lys Ile Ala Asp Tyr Asn Tyr Lys Leu Pro Asp Asp Phe
                    405                 410                 415

Thr Gly Cys Val Ile Ala Trp Asn Ser Asn Asn Leu Asp Ser Lys Val
                420                 425                 430

Gly Gly Asn Tyr Asn Tyr Leu Tyr Arg Leu Phe Arg Lys Ser Asn Leu
                435                 440                 445

Lys Pro Phe Glu Arg Asp Ile Ser Thr Glu Ile Tyr Gln Ala Gly Ser
            450                 455                 460

Thr Pro Cys Asn Gly Val Glu Gly Phe Asn Cys Tyr Phe Pro Leu Gln
465                 470                 475                 480

Ser Tyr Gly Phe Gln Pro Thr Asn Gly Val Gly Tyr Gln Pro Tyr Arg
                    485                 490                 495
```

```
Val Val Val Leu Ser Phe Glu Leu Leu His Ala Pro Ala Thr Val Cys
            500                 505                 510
Gly Pro Lys Ser Thr Asn Leu Val Lys Asn Lys Cys Val Asn Phe
        515                 520                 525
Asn Phe Asn Gly Leu Thr Gly Thr Gly Val Leu Thr Glu Ser Asn Lys
        530                 535                 540
Lys Phe Leu Pro Phe Gln Gln Phe Gly Arg Asp Ile Ala Asp Thr Thr
545                 550                 555                 560
Asp Ala Val Arg Asp Pro Gln Thr Leu Glu Ile Leu Asp Ile Thr Pro
                565                 570                 575
Cys Ser Phe Gly Gly Val Ser Val Ile Thr Pro Gly Thr Asn Thr Ser
                580                 585                 590
Asn Gln Val Ala Val Leu Tyr Gln Asp Val Asn Cys Thr Glu Val Pro
        595                 600                 605
Val Ala Ile His Ala Asp Gln Leu Thr Pro Thr Trp Arg Val Tyr Ser
        610                 615                 620
Thr Gly Ser Asn Val Phe Gln Thr Arg Ala Gly Cys Leu Ile Gly Ala
625                 630                 635                 640
Glu His Val Asn Asn Ser Tyr Glu Cys Asp Ile Pro Ile Gly Ala Gly
                645                 650                 655
Ile Cys Ala Ser Tyr Gln Thr Gln Thr Asn Ser Pro Gly Ser Ala Ser
                660                 665                 670
Ser Val Ala Ser Gln Ser Ile Ile Ala Tyr Thr Met Ser Leu Gly Ala
            675                 680                 685
Glu Asn Ser Val Ala Tyr Ser Asn Asn Ser Ile Ala Ile Pro Thr Asn
        690                 695                 700
Phe Thr Ile Ser Val Thr Thr Glu Ile Leu Pro Val Ser Met Thr Lys
705                 710                 715                 720
Thr Ser Val Asp Cys Thr Met Tyr Ile Cys Gly Asp Ser Thr Glu Cys
                725                 730                 735
Ser Asn Leu Leu Leu Gln Tyr Gly Ser Phe Cys Thr Gln Leu Asn Arg
                740                 745                 750
Ala Leu Thr Gly Ile Ala Val Glu Gln Asp Lys Asn Thr Gln Glu Val
            755                 760                 765
Phe Ala Gln Val Lys Gln Ile Tyr Lys Thr Pro Pro Ile Lys Asp Phe
        770                 775                 780
Gly Gly Phe Asn Phe Ser Gln Ile Leu Pro Asp Pro Ser Lys Pro Ser
785                 790                 795                 800
Lys Arg Ser Phe Ile Glu Asp Leu Leu Phe Asn Lys Val Thr Leu Ala
                805                 810                 815
Asp Ala Gly Phe Ile Lys Gln Tyr Gly Asp Cys Leu Gly Asp Ile Ala
                820                 825                 830
Ala Arg Asp Leu Ile Cys Ala Gln Lys Phe Asn Gly Leu Thr Val Leu
            835                 840                 845
Pro Pro Leu Leu Thr Asp Glu Met Ile Ala Gln Tyr Thr Ser Ala Leu
        850                 855                 860
Leu Ala Gly Thr Ile Thr Ser Gly Trp Thr Phe Gly Ala Gly Ala Ala
865                 870                 875                 880
Leu Gln Ile Pro Phe Ala Met Gln Met Ala Tyr Arg Phe Asn Gly Ile
                885                 890                 895
Gly Val Thr Gln Asn Val Leu Tyr Glu Asn Gln Lys Leu Ile Ala Asn
                900                 905                 910
```

-continued

```
Gln Phe Asn Ser Ala Ile Gly Lys Ile Gln Asp Ser Leu Ser Ser Thr
            915                 920                 925
Ala Ser Ala Leu Gly Lys Leu Gln Asp Val Val Asn Gln Asn Ala Gln
930                 935                 940
Ala Leu Asn Thr Leu Val Lys Gln Leu Ser Ser Asn Phe Gly Ala Ile
945                 950                 955                 960
Ser Ser Val Leu Asn Asp Ile Leu Ser Arg Leu Asp Pro Pro Glu Ala
                965                 970                 975
Glu Val Gln Ile Asp Arg Leu Ile Thr Gly Arg Leu Gln Ser Leu Gln
                980                 985                 990
Thr Tyr Val Thr Gln Gln Leu Ile Arg Ala Ala Glu Ile Arg Ala Ser
            995                 1000                1005
Ala Asn Leu Ala Ala Thr Lys Met Ser Glu Cys Val Leu Gly Gln
    1010                1015                1020
Ser Lys Arg Val Asp Phe Cys Gly Lys Gly Tyr His Leu Met Ser
    1025                1030                1035
Phe Pro Gln Ser Ala Pro His Gly Val Val Phe Leu His Val Thr
    1040                1045                1050
Tyr Val Pro Ala Gln Glu Lys Asn Phe Thr Thr Ala Pro Ala Ile
    1055                1060                1065
Cys His Asp Gly Lys Ala His Phe Pro Arg Glu Gly Val Phe Val
    1070                1075                1080
Ser Asn Gly Thr His Trp Phe Val Thr Gln Arg Asn Phe Tyr Glu
    1085                1090                1095
Pro Gln Ile Ile Thr Thr Asp Asn Thr Phe Val Ser Gly Asn Cys
    1100                1105                1110
Asp Val Val Ile Gly Ile Val Asn Asn Thr Val Tyr Asp Pro Leu
    1115                1120                1125
Gln Pro Glu Leu Asp Ser Phe Lys Glu Glu Leu Asp Lys Tyr Phe
    1130                1135                1140
Lys Asn His Thr Ser Pro Asp Val Asp Leu Gly Asp Ile Ser Gly
    1145                1150                1155
Ile Asn Ala Ser Val Val Asn Ile Gln Lys Glu Ile Asp Arg Leu
    1160                1165                1170
Asn Glu Val Ala Lys Asn Leu Asn Glu Ser Leu Ile Asp Leu Gln
    1175                1180                1185
Glu Leu Gly Lys Tyr Glu Gln Gly Tyr Ile Pro Glu Ala Pro Arg
    1190                1195                1200
Asp Gly Gln Ala Tyr Val Arg Lys Asp Gly Glu Trp Val Leu Leu
    1205                1210                1215
Ser Thr Phe Leu Gly His His His His His His
    1220                1225
```

ANTI-CORONAVIRUS VACCINES

CROSS-REFERENCE TO RELATED APPLICATIONS

This application claims the benefit of U.S. Provisional Application Nos. 63/064,225, filed Aug. 11, 2020, 63/088,708, filed Oct. 7, 2020 and 63/145,045, filed Feb. 3, 2021 the entire contents of which are incorporated herein by reference in their entirety.

FIELD OF THE INVENTION

This invention is in the field of recombinant coronavirus Spike proteins and immunogenic compositions containing same.

SEQUENCE LISTING

The instant application contains a Sequence Listing which has been submitted via EFS-Web as ASCII compliant text file format (.txt), and is hereby incorporated by reference in its entirety. The ASCII file was created on Oct. 7, 2020, is named "Sequence_Listing_000360_ST25" and has size of 37,849 bytes. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

BACKGROUND

Coronaviruses are a large family of viruses that can cause illnesses ranging widely in severity. The first known severe illness caused by a coronavirus emerged with the 2003 Severe Acute Respiratory Syndrome (SARS) epidemic in China. A second outbreak of severe illness began in 2012 in Saudi Arabia with the Middle East Respiratory Syndrome (MERS).

On December 31 of 2019, Chinese authorities alerted the World Health Organization of an outbreak of a novel strain of coronavirus causing severe illness, which was subsequently named SARS-CoV-2. SARS-CoV-2 is the virus that causes the disease referred to as COVID-19. As of Jul. 16, 2020, nearly 13.6 million COVID-19 cases have been documented worldwide, although many more mild cases have likely gone undiagnosed. The virus has killed over 585,000 people.

Shortly after the epidemic began, Chinese scientists sequenced the genome of SARS-CoV-2 and made the data available to researchers worldwide. The number of COVID-19 cases have been increasing because of human to human transmission after a single introduction into the human population.

SARS-CoV-2 spike proteins are located on the outside of the virus. The virus uses its spike protein to grab and penetrate the outer walls of human and animal cells. Scientists have focused on two distinctive features of SARS-CoV-2's spike protein—the Receptor Binding Domain (RBD) portion that binds to cells and the cleavage site that opens the virus up and allows it to enter host cells. The S1 and S2 subunits of the spike protein are responsible for receptor recognition and membrane fusion, respectively.

Scientists are still learning about this virus, but it appears that it can spread from people to animals in some situations, especially after close contact with a person sick with COVID-19.

Based on information available on the website of the Centers for Disease Control and Prevention (CDC), updated Jun. 22, 2020, we know that cats, dogs, and a few other types of animals can be infected with SARS-CoV-2, but we do not yet know all of the animals that can get infected. There have been reports of animals being infected with the virus worldwide.

A small number of pet cats and dogs have been reported to be infected with the virus in several countries, including the United States. Most of these pets became sick after contact with people with COVID-19. Several lions and tigers at a New York zoo tested positive for SARS-CoV-2 after showing signs of respiratory illness. Public health officials believe these large cats became sick after being exposed to a zoo employee who was infected with SARS-CoV-2.

SARS-CoV-2 was recently discovered in mink (which are closely related to ferrets) on multiple farms in the Netherlands. The mink showed respiratory and gastrointestinal signs; the farms also experienced an increase in mink deaths. Because some workers on these farms had symptoms of COVID-19, it is likely that infected farm workers were the source of the mink infections. Some farm cats on several mink farms also developed antibodies to this virus, suggesting they had been exposed to the virus at some point.

The CDC, U.S. Department of Agriculture (USDA), and state public health and animal health officials are working in some states to conduct active surveillance of SARS-CoV-2 in pets, including cats, dogs, and other small mammals, that had contact with a person with COVID-19. These animals are being tested for SARS-CoV-2 infection, as well as tested to see whether the pet develops antibodies to this virus. This work is being done to help us better understand how common SARS-CoV-2 infection might be in pets as well as the possible role of pets in the spread of this virus. The USDA maintains a list of cases of SAR-CoV-2 (the same virus that causes COVID-19 in humans) in animals in the United States that have been confirmed by the USDA's National Veterinary Services Laboratories.

The development of human vaccines against SARS-CoV-2 is underway but a veterinary vaccine is also needed.

SUMMARY OF INVENTION

In the first aspect, the invention provides a composition comprising a coronavirus, a Spike protein of said coronavirus or an immunogenic fragment of said Spike protein, and an adjuvant comprising a saponin, a sterol, and a CpG-containing immunostimulatory oligonucleotide. In certain embodiments of this first aspect, the adjuvant consists essentially or consists of the saponin, the sterol, and the CpG-containing immunostimulatory oligonucleotide. In any of the embodiments described above, the saponin may be a triterpenoid saponins, preferably extracted from bark of *Quillaia Saponaria*, and the sterol may be selected from the group consisting of β-sitosterol, stigmasterol, ergosterol, ergocalciferol, and cholesterol. In any of the embodiments described above, the saponin may be present in the amount of about 20 µg per dose and the sterol may be present in the amount of about 20 µg per dose.

In the second aspect, the invention provides a composition comprising coronavirus, a Spike protein from said coronavirus or an immunogenic fragment of said Spike protein, and an adjuvant comprising (or consisting essentially of or consisting) a CpG containing immunostimulatory oligonucleotide and a glycolipid according to Formula I,

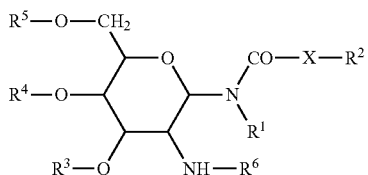

Formula I wherein, $R^1$ is hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, —$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

In certain embodiments of this second aspect, the glycolipid is N-(2-Deoxy-2-L-leucylamino-β-D-glucopyranosyl)-N-octadecyldodecanoylamide or a salt thereof, such as an acetate thereof. In any of the embodiments of this second aspect of the invention, the glycolipid may be present in the amount of about 250 µg per dose.

In any of the embodiments of the first and/or the second aspect of the invention as described above, the immunostimulatory oligonucleotide may be a P-class immunostimulatory oligonucleotide characterized by the presence of one or more TLR-9 activating motif (s) and two palindromes or two complementarity areas. Preferably, said P-class immunostimulatory oligonucleotide is 5' modified, and more preferably, wherein said P class immunostimulatory oligonucleotide comprises at least 22 contiguous nucleotides of SEQ ID NO: 8. In certain embodiments of the first and/or the second aspect of the invention, the CpG containing immunostimulatory oligonucleotide is present in the amount of about 20 to about 50 µg per dose.

In a third aspect, the invention provides a composition comprising a coronavirus, a Spike protein from said coronavirus or an immunogenic fragment of said Spike protein, and an adjuvant comprising a saponin, a sterol, a quaternary ammonium compound, and a polyacrylic acid polymer. In certain embodiments of this third aspect of the invention, the saponin is a triterpenoid saponin, preferably extracted from the bark of *Quillaia Saponaria*, such as is Quil A and the sterol is selected from the group consisting of β-sitosterol, stigmasterol, ergosterol, ergocalciferol, and cholesterol, and the quaternary ammonium compound is DDAB. In certain embodiments, said Quil A is present in the amount of about 20 μg per dose, the sterol is cholesterol and is present in the amount of about 20 μg per dose, the DDAB is present in the amount of about 10 μg per dose, and the polyacrylic acid polymer is present in the amount of about 0.05% v/v.

In certain embodiments of the first, the second, or the third aspect of the invention, the coronavirus is SARS-2 coronavirus and the antigen is the Spike protein or the immunogenic fragment thereof. In certain embodiments applicable to the first, the second and the third aspect of the invention, wherein the Spike protein is at least 90% identical to SEQ ID NO: 13, with a proviso that said protein is in a pre-fusion state. In certain embodiments, the pre-fusion state is conferred by substitution of amino acids at position 973 and/or 974 of SEQ ID NO: 13. In certain preferred embodiments, the amino acids at positions 973 and 974 are substituted to prolines.

In certain embodiments, applicable to any of the above-described embodiments, spike protein or the fragment thereof comprises a mutation in SEQ ID NO: 15, preferably, a mutation wherein SEQ ID NO: 15 is replaced with SEQ ID NO: 16. In further embodiments, applicable to all spike proteins or fragments thereof described above, the protein may further comprise a foldon sequence such as, for example SEQ ID NO:12. In certain embodiments, the composition according to the first, the second, or the third aspect of the invention comprises a spike protein or an immunogenic fragment thereof in the amount of about 20 μg per dose.

The fourth aspect of the invention provides a method of inducing an immune response in a subject in need thereof, the method comprising administering to said subject the composition according to any one the embodiments described above.

In certain embodiments of this fourth aspect, wherein said immunogenic composition is administered to said subject in a prime administration and in a boost administration, wherein the boost administration is between about 14 and about 42 days after the prime administration.

Preferably, the immune response is a protective immune response and, in certain embodiments, said protective immune response is retained for sixth or twelve months after the prime vaccination.

In certain embodiments of this fourth aspect, said subject is a canine and the adjuvant in said immunogenic composition comprises the saponin, the sterol, and the CpG-containing immunostimulatory oligonucleotide. In other embodiments, said subject is a feline and the adjuvant in said immunogenic composition comprises the CpG-containing immunostimulatory oligonucleotide and the glycolipid according to Formula I. In yet other embodiments, said subject is a feline and the adjuvant in said immunogenic composition comprises the sterol, the saponin, the quaternary ammonium compound and the polyacrylic acid polymer.

DETAILED DESCRIPTION

Definitions

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater. With regard to time period, the term "about" refers to the indicated value and to a range within 10% of the indicated value (e.g., "about 8 months" includes 8 months as well as 8 months plus or minus 10%), except the upper limit of "about 11 months" is 12 months and the upper limit of "about 12 months" is 12.5 months.

"Adjuvant" means any substance that increases the humoral or cellular immune response to an antigen. Adjuvants are generally used to accomplish two objectives: the controlled release of antigens from the injection site, and the stimulation of the immune system.

"Antibody" refers to an immunoglobulin molecule that can bind to a specific antigen as the result of an immune response to that antigen. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions.

"Antigen" or "immunogen" refers to any substance that is recognized by the animal's immune system and generates an immune response. The term includes killed, inactivated, attenuated, or modified live bacteria, viruses, or parasites. The term "antigen" also includes polynucleotides, polypeptides, recombinant proteins, synthetic peptides, protein extract, cells (including tumor cells), tissues, polysaccharides, or lipids, or fragments thereof, individually or in any combination thereof. The term antigen also includes antibodies, such as anti-idiotype antibodies or fragments thereof, and to synthetic peptide mimotopes that can mimic an antigen or antigenic determinant (epitope).

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

"Conservative substitutions" refer to replacement of one amino acid with another amino acids, wherein the replacing and the replaced amino acid have similar structures. For example, changes which result in the substitution of one negatively charged residue for another, such as aspartic acid for glutamic acid, or one positively charged residue for another, such as lysine for arginine, can also be expected to produce a protein with substantially the same functional activity.

The following six groups each contain amino acids that are typical conservative substitutions for one another: [1] Alanine (A), Serine (S), Threonine (T); [2] Aspartic acid (D), Glutamic acid (E); [3] Asparagine (N), Glutamine (Q); [4] Arginine (R), Lysine (K), Histidine (H); [5] Isoleucine (I), Leucine (L), Methionine (M), Valine (V); and [6] Phenylalanine (F), Tyrosine (Y), Tryptophan (W), (see, e.g., US Patent Publication 20100291549).

"Consisting essentially" as applied to the adjuvant formulations refers to formulation which does not contain unrecited additional adjuvanting or immunomodulating agents in the amounts at which said agent exert measurable adjuvanting or immunomodulating effects. Preferably, if present, such unrecited additional adjuvanting or immunomodulating agents are in the amount that is below detection threshold.

"Dose" refers to a vaccine or immunogenic composition given to a subject in a single administration "Immune response" in a subject refers to the development of a humoral immune response, a cellular immune response, or a humoral and a cellular immune response to an antigen. Immune responses can usually be determined using standard immunoassays, cell-based assays, and neutralization assays, which are known in the art.

"Immunologically effective amount" or "effective amount to produce an immune response" of an antigen is an amount effective to induce an immunogenic response in the recipient. The immunogenic response may be sufficient for diagnostic purposes or other testing or may be adequate to prevent signs or symptoms of disease, including adverse health effects or complications thereof, caused by infection with a disease agent. Either humoral immunity or cell-mediated immunity or both may be induced. The immunogenic response of an animal to an immunogenic composition may be evaluated, e.g., indirectly through measurement of antibody titers, cytokine assays, lymphocyte proliferation assays, or directly through monitoring signs and symptoms after challenge with wild type strain, whereas the protective immunity conferred by a vaccine can be evaluated by measuring, e.g., reduction in clinical signs such as mortality, morbidity, temperature number, overall physical condition, and overall health and performance of the subject. The immune response may comprise, without limitation, induction of cellular and/or humoral immunity.

"Immunogenic" means evoking an immune or antigenic response. Thus, an immunogenic composition would be any composition that induces an immune response.

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio, and effective for their intended use.

The term "protective immune response" refers to the immune response, elicited by an immunogenic composition or a vaccine in a subject, wherein upon the challenge with the coronavirus against which the animal was immunized, the subject does not get infected (complete protection) or exhibits symptoms of lesser magnitude and/or duration compared to the non-immunized animal (partial protection). In a particularly preferred embodiment of partial protection, the immunized and challenged subject does not shed the coronavirus, or the magnitude and/or the duration of shedding is decreased. Thus, protective immune response prevents the infection and/or lessens the symptoms and/or the duration of the infection.

The term "sequence identity" refers to identity between two sequences within a comparison window. Protein sequence identities can be evaluated using any of the variety of sequence comparison algorithms and programs known in the art. For sequence comparison, typically one sequence acts as a reference sequence (e.g., a sequence disclosed herein), to which test sequences are compared. A sequence comparison algorithm then calculates the percent sequence identities for the test sequences relative to the reference sequence, based on the program parameters.

The percent identity of two amino acid sequences can be determined for example by comparing sequence information using the computer program GAP, i.e., Genetics Computer Group (GCG; Madison, WI) Wisconsin package version 10.0 program, GAP (Devereux et al. (1984), Nucleic Acids Res. 12: 387-95). In calculating percent identity, the sequences being compared are typically aligned in a way that gives the largest match between the sequences. The preferred default parameters for the GAP program include: (1) The GCG implementation of a unary comparison matrix (containing a value of 1 for identities and 0 for non-identities) for nucleotides, and the weighted amino acid comparison matrix of Gribskov and Burgess, ((1986) Nucleic Acids Res. 14: 6745) as described in *Atlas of Polypeptide Sequence and Structure*, Schwartz and Dayhoff, eds., National Biomedical Research Foundation, pp. 353-358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps.

Sequence identity and/or similarity can also be determined by using the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (BESTFIT, FASTA, and TFASTA in the Wisconsin Genetics Software Package, Genetics Computer Group, 575 Science Dr., Madison, WI).

Another example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

The term "subject" refers to organisms susceptible to being infected with a given coronavirus and may be represented by different species of birds and mammals, including, without limitations, humans and non-human mammals. Thus, subjects susceptible to avian infectious bronchitis include poultry, subjects susceptible to Porcine Epidemic Diarrhea include swine, and subjects susceptible to SARS CoV-2 include cats, dogs, Mustellidae (ferrets, sabers, minks, weasels) and humans.

The term "treating" refers to reducing or alleviating magnitude and/or duration of at least one symptom of an existing coronavirus infection.

The term "vaccine" refers to an immunogenic composition that elicits protective immune response in the subject. when administered to a subject, induces or stimulates a protective immune response. A vaccine can render an organism immune to a particular disease, in the present case coronavirus infection, and more particularly SARS-CoV-2 infection. The vaccine of the present invention thus induces an immune response in a subject which is protective against subsequent SARS-CoV-2 challenge. A vaccine comprising the antigen and the adjuvant of the invention may be capable of inducing a cross-protective immune response against a plurality of coronavirus genotypes.

Antigens

The antigen used in the compositions described herein is an inactivated coronavirus or Spike protein of the coronavirus or an immunogenic fragment of said Spike protein.

Multiple coronaviruses are suitable for the use in the compositions described herein. These coronaviruses include, without limitations, Porcine Epidemic Diarrhea Virus (PEDV), Swine Delta Coronavirus (CoV), Feline Infectious Peritonitis Virus, Feline Enteric CoV, Avian Infectious Bronchitis Virus, Turkey CoV, Canine CoV, Canine Respiratory CoV, Bovine CoV, Equine CoV, TGEV, Porcine Respiratory CoV, Porcine Hemagglutinating Encephalomyelitis Virus.

In certain embodiments, the recombinant spike protein antigen comprises a wild-type 2019-nCoVS protein having the amino acid sequence of SEQ ID NO: 11 or a sequence that is at least 80% identical thereto (e.g., at least 85% or at least 90% or at least 91% or at least 92% or at least 93% or at least 94% or at least 95% or at least 96% or at least 97% or at least 98% or at least 99% or at least 99.5% identical to SEQ ID NO: 11), with a proviso that the protein is in a prefusion conformation. Sequence identity should be determined without considering the N-terminal signal peptide "MFVFLVLLPLVSS" (SEQ ID NO: 14).

In certain embodiments, the prefusion conformation is achieved by introducing mutations between Heptad Repeat 1 and Central Helix of SEQ ID NO: 11 (or a sequence at least 80% identical thereto as discussed above). Amino acids at positions 986 and 987 of SEQ ID NO: 11 are particularly suitable for the mutations. In certain embodiments amino acids 986 and 987 are both replaced with proline.

In certain embodiments, furin cleavage site PRRARS (SEQ ID NO: 15) that is generally present between the S1 and S2 domains of the spike protein is mutated so that furin does not cleave the antigen. In certain embodiments, SEQ ID NO: 15 is mutated into SEQ ID NO: 16 (PGSASS).

In certain embodiments, the recombinant spike protein comprises a C-terminal T4 fibritin foldon motif, such as "GYIPEAPRGDQAYVRKDGEWVLLSTFL" (SEQ ID NO: 12), and, optionally, a purification tag such as a C-terminal polyhistidine tag.

In a preferred embodiment, amino acids of the recombinant spike protein according to the invention corresponding to amino acids at positions 986 and 987 of SEQ ID NO: 11 are proline residues, the furin cleavage site is mutated into SEQ ID NO: 16, the protein comprises the foldon sequence of SEQ ID NO: 12 and the C-terminal polyhistidine purification tag.

In certain embodiments, the amino acids differing between the recombinant spike protein are conservative substitutions.

In another embodiment, the antigen is a fragment of the wild-type 2019-nCoVS protein, as described above, with a proviso that the fragment comprises both comprising the S1 and S2 domains.

In certain embodiments, the fragment corresponds to residues 14 to 1208 of the wild-type 2019-nCoVS protein of SEQ ID NO: 11, as provided in SEQ ID NO: 13, or a sequence that is at least 80% identical thereto (e.g., at least 85% or at least 90% or at least 91% or at least 92% or at least 93% or at least 94% or at least 95% or at least 96% or at least 97% or at least 98% or at least 99% or at least 99.5% identical to SEQ ID NO: 13), with a proviso that the protein is in a prefusion conformation, and, optionally, with a further proviso that the furin cleavage site of said fragment is non-functional. As described above, the pre-fusion conformation may be achieved by substituting residues 973 and/or 974 of SEQ ID NO: 13 (corresponding to residues 986 and 987 of SEQ ID NO: 11). The preferred substitution will entail proline residues at both positions.

The fragment may further comprise foldon and/or an immunopurification tag, as described above. In certain embodiments, the fragment of the Spike protein of a coronavirus is a conservatively substituted variant of SEQ ID NO: 13. In the most preferred embodiment, the antigen comprises (or consists of) SEQ ID NO: 17.

Methods of preparing the antigen according to the invention are well known. For example, genetic engineering techniques and recombinant DNA expression systems may be used.

Nucleic acid molecules encoding the amino acid sequences of the antigen according to any embodiment of the invention may also be inserted into a vector (e.g., a recombinant vector) such as one or more non-viral and/or viral vectors. Non-viral vectors may include, for instance, plasmid vectors (e.g., compatible with bacterial, insect, and/or mammalian host cells). Exemplary vectors may include, for example, PCR-ii, PCR3, and pcDNA3.1 (Invitrogen, San Diego, Calif.), pBSii (Stratagene, La Jolla, Calif.), pet15 (Novagen, Madison, Wis.), pGEX (Pharmacia Biotech, Piscataway, N.J.), pEGFp-n2 (Clontech, Palo Alto, Calif.), pET1 (Bluebacii, Invitrogen), pDSR-alpha (PCT pub. No. WO 90/14363) and pFASTBACdual (Gibco-BRL, Grand island, NY) as well as Bluescript plasmid derivatives (a high copy number COLe1-based phagemid, Stratagene Cloning Systems, La Jolla, Calif.), PCR cloning plasmids designed for cloning TAQ-amplified PCR products (e.g., TOPO™ TA Cloning® kit, PCR2.1® plasmid derivatives, Invitrogen, Carlsbad, Calif.). Bacterial vectors may also be used including, for instance, *Shigella, Vibrio cholerae, Lactobacillus, Bacille Calmette Guerin* (BCG), and *Streptococcus* (see for example, WO 88/6626; WO 90/0594; WO 91/13157; WO 92/1796; and WO 92/21376). The vectors may be constructed using standard recombinant techniques widely available to one skilled in the art. Many other non-viral plasmid expression vectors and systems are known in the art and may be used.

Various viral vectors that have been successfully utilized for introducing a nucleic acid to a host include retrovirus, adenovirus, adeno-associated virus (AAV), herpes virus, baculovirus, and poxvirus, among others. Viral vectors may be constructed using standard recombinant techniques widely available to one skilled in the art. See, e.g., *Molecular cloning: a laboratory manual* (Sambrook & Russell: 2000, Cold Spring Harbor Laboratory Press; ISBN: 0879695773), and: *Current protocols in molecular biology* (Ausubel et al., 1988+ updates, Greene Publishing Assoc., New York; ISBN: 0471625949). The vectors may be used to infect host cells, such as, for example, a bacterium, a yeast cell (e.g., a Pichia cell), an insect cell, or a mammalian cell (e.g., CHO cell), and the expressed proteins can be harvested and purified according to the methods known in the art.

Expression of the amino acid sequences of the antigens recited herein may also be performed in so-called cell-free expression systems. Such systems comprise all essential factors for expression of the nucleic acid encoding the antigens, operably linked to a promoter that is capable of expression in that particular system. Examples are the *E. coli* lysate system (Roche, Basel, Switzerland), or the rabbit reticulocyte lysate system (Promega corp., Madison, USA).

In certain embodiments, SEQ ID NO: 17 is prepared by expressing an amino acid sequence comprising SEQ ID NO: 17 and the signal peptide of SEQ ID NO: 14 upstream of SEQ ID NO: 17. SEQ ID NO: 14 is cleaved off during the processing.

The antigen according to any of the embodiments may be present in the immunogenic compositions recited herein in the immunologically effective amount, sufficient to cause immune response, and preferably, protective immune response. Generally, the immunologically effective amount is the amount of between about 1 μg and 1 mg per dose. In the embodiments where the recombinant spike protein or a fragment thereof is the antigen, the protein or the fragment thereof may be present in the amount of about 1 μg to about 500 μg per dose, or between about 1 μg and about 200 μg, or between about 2 μg and about 100 μg or between about 5 μg and about 50 μg, or between about 10 μg and about 25 μg, or about 20 μg.

Adjuvants

Multiple adjuvanting compounds are known in the art, including, without limitations, saponins, sterols, quaternary ammoniums, glycolipids stimulating Th2 response, polymers, especially, polymers of a polyacrylic acid, and immunostimulatory oligonucleotides.

Saponins

Suitable saponins include triterpenoid saponins. These triterpenoids a group of surface-active glycosides of plant origin and share common chemical core composed of a hydrophilic region (usually several sugar chains) in association with a hydrophobic region of either steroid or triterpenoid structure. Because of these similarities, the saponins sharing this chemical core are likely to have similar adjuvanting properties. Triterpenoids suitable for use in the adjuvant compositions can come from many sources, either plant derived or synthetic equivalents, including but not limited to, *Quillaja saponaria*, tomatine, ginseng extracts, mushrooms, and an alkaloid glycoside structurally similar to steroidal saponins.

If a saponin is used, the adjuvant compositions generally contain an immunologically active saponin fraction from the bark of *Quillaja saponaria*. The saponin may be, for example, Quil A or another purified or partially purified saponin preparation, which can be obtained commercially. Thus, saponin extracts can be used as mixtures or purified individual components such as QS-7, QS-10, QS-17, QS-18, and QS-21. In one embodiment the Quil A is at least 85% pure. In other embodiments, the Quil A is at least 90%, 91%, 92%, 93%, 94%, 95%, 96%, 97%, 98%, or 99% pure.

If the triterpenoid saponin (e.g., Quil A or a purified fraction hereof) may be present in the vaccine, then in certain embodiments, one dose of the vaccine may contain 1-1000 μg of said triterpenoid saponin, or 10-100, or 5-50 or 1-25, or 25-300 or 50-200 or 50-100 μg per dose. For neonates smaller animals (e.g., dogs or cats or minks), the amount may be between about 1 and about 100 μg per dose (e.g., between about 5 and about 50 μg per dose, or between about 10 and about 25 μg per dose, or between about 15 and about 20 μg per dose), and for larger animals (e.g., horses, pigs, or cattle) the amount may be between about 50 and about 1000 μg per dose.

Sterols

Sterols share a common chemical core, which is a steroid ring structure[s], having a hydroxyl (OH) group, usually attached to carbon-3. The hydrocarbon chain of the fatty-acid substituent varies in length, usually from 16 to 20 carbon atoms, and can be saturated or unsaturated. Sterols commonly contain one or more double bonds in the ring structure and also a variety of substituents attached to the rings. Sterols and their fatty-acid esters are essentially water-insoluble. In view of these chemical similarities, it is thus likely that the sterols sharing this chemical core would have similar properties when used in the vaccine compositions of the instant invention. Sterols are well known in the art and can be purchased commercially. For example, cholesterol is disclosed in the Merck Index, 12th Ed., p. 369. Suitable sterols include, without limitations, β-sitosterol, stigmasterol, ergosterol, ergocalciferol, and cholesterol.

If the sterol may be present in the vaccine, then in certain embodiments, one dose of the vaccine may contain 1-1000 µg of said sterol. In different embodiments, the amount of the sterol is 10-100, or 5-50 or 1-25, or 25-300 or 50-200 or 50-100 µg per dose. For neonates or smaller animals (e.g., dogs or cats or minks), the amount may be between about 1 and about 100 µg per dose (e.g., between about 5 and about 50 µg per dose, or between about 10 and about 25 µg per dose, or between about 15 and about 20 µg per dose), and for larger animals (e.g., horses, pigs, or cattle) the amount may be between about 50 and about 1000 µg per dose.

CpG-Containing Immunostimulatory Oligonucleotides

The adjuvant component of the vaccine also comprises an immunostimulatory oligonucleotide. Immunomodulatory oligonucleotides according to the invention comprise CpG (and are also referred to as "CpG containing immunostimulatory oligonucleotides", "CpG oligonucleotides" or simply "CpGs"). The effect of CpG containing oligonucleotides on the immune system has been known for over 20 years.

Generally, the CpGs suitable for the invention are between 15 and 100 bases long, e.g., between 15 and 50 bases long, or between 18 and 40 bases long or between 20 and 30 bases long, or 20-24 bases long.

Several classes of CpG have been described, including A-class CpGs, B-class CpGs, C-class CpGs, and P-class CpGs. In certain embodiments, the CpG containing immunostimulatory oligonucleotide is a P-class CpG. P-class CpGs are characterized by the presence of one or more TLR-9 activating motif(s) and two palindromes or two complementarity areas. Preferably, the one or more TLR-9 activating motifs are at the 5' of the oligonucleotide and may be completely or partially be incorporated into the 5' palindrome or the 5' complementarity area. TLR-9 activating motifs are known and include, without limitations, TCG, TTCG, TTTCG, TYpR, TTYpR, TTTYpR, UCG, UUCG, UUUCG, TTT, or TTTT. The 5' palindrome or the 5' complementarity area is at least 6 bases long. The 3' palindrome or the 3' complementarity area is at least 8 bases long and is generally rich in C and G. These structural features of the P-class CpGs confer the ability to spontaneously self-assemble into concatamers either in vitro and/or in vivo.

In order to increase lipophilicity of the CpG oligonucleotides, at least one lipophilic substituted nucleotide analog may be included, preferably at the 5' end of the oligonucleotide. The P-class immunostimulatory oligonucleotides may be modified according to techniques known in the art. For example, J-modification refers to iodo-modified nucleotides. E-modification refers to ethyl-modified nucleotide(s). Thus, E-modified P-class immunostimulatory oligonucleotides are P-class immunostimulatory oligonucleotides, wherein at least one nucleotide (preferably 5' nucleotide) is ethylated. Additional modifications include attachment of 6-nitro-benzimidazol, 0-Methylation, modification with proynyl-dU, inosine modification, 2-bromovinyl attachment (preferably to uridine).

The oligonucleotides modified by an addition of a lipophilic moiety are generally described in US 20100166780.

In certain embodiments, CpGs according to the invention comprise the modified backbone including, without limitations, phosphorothioate modifications, halogenations, alkylation (e.g., ethyl- or methyl-modifications), and phosphodiester modifications.

Suitable non-limiting examples of modified P-class immunostimulatory oligonucleotides are provided below ("*" refers to a phosphorothioate bond, "-" refers to a phosphodiester bond, "JU" refers to 5'-Iodo-2'-deoxyuridine and "EU" refers to 5-Ethyl-2'-deoxyuridine).

```
                                                SEQ ID NO: 1
5' T*C-G*T*C-G*A*C-G*A*T*C-G*G*C*G*C-G*C*G*C*C*G
3'

SEQ ID NO: 2
5' T*C-G*A*C*G*T*C*G*A*T*C*G*G*C*G*C*G*C*G*C*C*G
3'

SEQ ID NO: 3
5' T*C*G*A*C*G*T*C*G*A*T*C*G*G*C*G*C*G*C*G*C*C*G*T
3'

SEQ ID NO: 4
5' JU*C-G*A*C*G*T*C*G*A*T*C*G*G*C*G*C*G*C*G*C*C*G
3'

SEQ ID NO: 5
5' JU*C-G*A*C*G*T*C*G*A*T*C*G*G*C*G*C*G*C*G*C*C*G*
T3'

SEQ ID NO: 6
5' JU*C*G*A*C*G*T*C*G*A*T*C*G*G*C*G*C*G*C*G*C*C*G*
T3'

SEQ ID NO: 7
5' EU*C-G*A*C*G*T*C*G*A*T*C*G*G*C*G*C*G*C*G*C*C*G
3'

SEQ ID NO: 8
5' JU*C-G*T*C*G*A*C*G*A*T*C*G*G*C*G*G*C*C*G*C*C*G*
T3'

SEQ ID NO: 9
5' JU*C*G*T*C*G*A*C*G*A*T*C*G*G*C*G*G*C*C*G*C*C*G*
T3'

SEQ ID NO: 10
5' T*C-G*T*C-G*A*C-G*A*T*C-G*G*C*G*C-G*C*G*C*C*G
3'
```

In certain embodiments, the CpG oligonucleotide according to the invention comprises any one of SEQ ID NOs 1-10 or an oligonucleotide comprising at least 15 consecutive bases of any one of SEQ ID NOs 1-10. In the most preferred embodiment, the vaccine comprises an oligonucleotide comprising at least 15 consecutive bases of SEQ ID NO: 8 (e.g., at least 16, at least 17, at least 18, at least 19, at least 20, at least 21, at least 22, or at least 23).

The CpG oligonucleotide may be present in the vaccine in the amount of 10-400 µg per dose of the vaccine, or 25-300 or 50-200 or 50-100 µg per dose. For neonates or smaller animals (e.g., dogs or cats or minks), the amount may be between about 0.5 µg and about 70 µg per dose (e.g., between about 2 µg and about 40 µg per dose or between about 5 µg and about 30 µg per dose or between about 10 µg and about 25 µg per dose, or about 20 µg per dose), and for larger animals (e.g., horses, pigs, or cattle) the amount may be between about 50 µg and about 400 µg per dose (e.g., between about 100 µg and about 300 µg per dose, or between about 150 µg and about 250 µg per dose).

Polyacrylic Acid Polymers

Polyacrylic acid polymers are also suitable adjuvanting compounds. For example, CARBOPOL® polymers are polymers of acrylic acid cross-linked with polyalkenyl ethers or divinyl glycol. CARBOPOL® has been used in a number of vaccines.

The polyacrylic polymer may be present in the vaccine in the amount of 0 to about 30% v/v, e.g., about 0.001% v/v to about 25% v/v, of about 0.005% v/v to about 15% v/v, of about 0.01% v/v to about 10% v/v, of about 0.05% v/v to about 1% v/v, and of about 0.05% v/v to about 0.25% v/v.

Glycolipids

Suitable glycolipids are generally those which activate the Th2 response. The glycolipids include, without limitations, those encompassed by Formula I and that are generally described in US Patent Publication 20070196384 (Ramasamy et al).

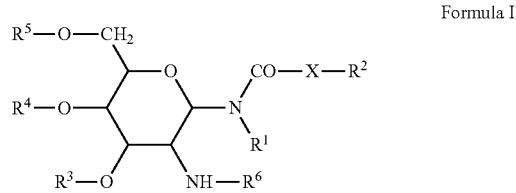

Formula I wherein, $R^1$ is hydrogen, or a saturated alkyl radical having up to 20 carbon atoms; X is —$CH_2$—, —O— or —NH—; $R^2$ is hydrogen, or a saturated or unsaturated alkyl radical having up to 20 carbon atoms; $R^3$, $R^4$, and $R^5$ are independently hydrogen, —$SO_4^{2-}$, -$PO_4^{2-}$, —$COC_{1-10}$ alkyl; $R^6$ is L-alanyl, L-alpha-aminobutyl, L-arginyl, L-asparginyl, L-aspartyl, L-cysteinyl, L-glutamyl, L-glycyl, L-histidyl, L-hydroxyprolyl, L-isoleucyl, L-leucyl, L-lysyl, L-methionyl, L-ornithinyl, L-phenyalany, L-prolyl, L-seryl, L-threonyl, L-tyrosyl, L-tryptophanyl, and L-valyl or their D-isomers.

Examples of a glycolipid are, without limitation, N-(2-Deoxy-2-L-leucylamino-β-D-glucopyranosyl)-N-octadecyldodecanoylamide (BayR® 1005, or R1005) or a salt (e.g., an acetate) thereof.

If the glycolipid may be present in the vaccine, then in different embodiments, one dose of the vaccine may contain 0.01 mg to about 10 mg per dose mg of the glycolipid. Thus, for example, the glycolipid may be present in the amount of about 0.05 to 2 mg per dose, or about 1 to about 5 mg per dose or about 4 to about 8 mg per dose or about 5 to about 10 mg per dose. For neonates or smaller animals (e.g., dogs or cats or minks or weasels, the amount may be between about 0.1 and about 1 mg per dose (e.g., about 0.25 to about 0.75 mg per dose, or about 0.2 mg per dose to 0.4 mg per dose), and for larger animals (e.g., horses, pigs, or cattle) the amount may be between about 1 and about 10 mg per dose.

Quaternary Ammonium Compounds

Quaternary ammonium compounds are ammonium-based compounds with four hydrocarbon groups. In practice, hydrocarbon groups are generally limited to alkyl or aryl groups. In a set of embodiments, the quaternary ammonium compounds are composed of four alkyl chains, two of which are C10-C20 alkyls and the remaining two are C1-C4 alkyls. In certain embodiments, the quaternary ammonium is dimethyldioctadecylammonium (DDA) bromide, chloride or another pharmaceutically acceptable counter ion.

If the quaternary ammonium compound is present in the vaccine, one dose of the vaccine may contain the quaternary ammonium in amount of 1-1000 µg, or 1-1000 µg, 1-500 µg or 10-100 µg, or 5-50 µg or 1-25 µg, or 25-300 µg or 50-200 µg or 50-100 µg. For neonates or smaller animals (e.g., dogs or cats or minks), the amount may be between about 1 mg and about 100 mg per dose (e.g., between about 5 µg and about 50 µg per dose, or between about 10 µg and about 25 µg per dose, or between about 15 µg and about 20 µg per dose), and for larger animals (e.g., horses, pigs, or cattle) the amount may be between about 50 µg and about 1000 µg per dose.

In certain embodiments, the adjuvant generally comprises (or consists of) a combination of a triterpenoid saponin, a sterol, and a CpG-containing immunostimulatory oligonucleotide. Optionally, the adjuvant may further comprise effective amounts of the quaternary ammonium, the glycolipid and/or the polyacrylic acid polymer such as CARBOPOL®. In certain embodiments, the adjuvant lacks effective amounts (or any detectable amounts) of a quaternary ammonium compound, e.g., avridine or DDAB, a polyacrylic acid polymer such as, for example CARBOPOL® and/or the. In certain embodiments, in one dose of this adjuvant, Quil A is present in the amount of about 10 µg to about 300 µg, cholesterol is present in the amount of between about 10 µg and about 300 µg, and CpG-containing immunostimulatory oligonucleotide is present in the amount of between 10 µg and 250 µg. Preferably, the CpG-containing immunostimulatory oligonucleotide consists of or comprises SEQ ID NO: 8.

In embodiments particularly suitable for canines, Quil A may be present in the amount of between 10 µg and 50 µg (preferably between about 15 µg and 25 µg, or at about 20 µg), cholesterol may be present in the amount of between 10 µg and 50 µg (preferably between about 15 µg and 25 µg, or at about 20 µg), and the CpG-containing immunostimulatory oligonucleotide may be present in the amount of between about 10 µg and about 50 µg (preferably between about 15 µg and about 25 µg, or at about 20 µg).

In other embodiments, the adjuvant comprises (or consists of) a combination of the CpG-containing immunostimulatory oligonucleotide and the glycolipid according to Formula I. In certain embodiments, the adjuvant lacks effective amounts (or any detectable amounts) of a quaternary ammonium compound, e.g., avridine or DDAB, a polyacrylic acid polymer such as, for example CARBOPOL® and/or a triterpenoid saponin, especially a saponin from Q. Saponaria (including Quil A and fractions thereof). In certain embodiments, one dose of this adjuvant contains between about 15 and about 100 µg of the CpG-containing immunostimulatory oligonucleotide and between about 100 and about 1000 µg per dose (e.g., about 250 to about 750 µg per dose, or about 200 µg per dose to 400 µg per dose) of the glycolipid according to Formula I as described above, which, preferably is N-(2-Deoxy-2-L-leucylamino-β-D-glucopyranosyl)-N-octadecyldodecanoylamide or a salt (e.g., acetate) thereof. Preferably, the CpG-containing immunostimulatory oligonucleotide consists of or comprises SEQ ID NO: 8.

In yet other embodiments, the adjuvant contains Quil A, Cholesterol, DDAB, and CARBOPOL®. In certain embodiments particularly suitable for felines and Mustellidae animals, Quil A may be present in the amount of between 10 µg and 50 µg (preferably between about 15 µg and 25 µg, or at about 20 µg), cholesterol may be present in the amount of between 10 µg and 50 µg (preferably between about 15 µg and 25 µg, or at about 20 µg), DDAB may be present in the amount of between about 5 µg and 20 µg, or between about 10 µg and about 15 µg, or about 10 µg, and CARBOPOL® is present in the amount of about 0.01% to about 0.1%, or about 0.05% v/v.

Excipients

Other components of the compositions can include pharmaceutically acceptable excipients, such as carriers, solvents, and diluents, isotonic agents, buffering agents, stabilizers, preservatives, antibacterial agents, antifungal agents, and the like. Typical carriers, solvents, and diluents include water, saline, dextrose, ethanol, glycerol, oil, and the like. Representative isotonic agents include sodium chloride, dextrose, mannitol, sorbitol, lactose, and the like. Useful stabilizers include gelatin, albumin, and the like. The compositions can also contain antibiotics or preservatives, including, for example, gentamicin, merthiolate, or chlorocresol. The various classes of antibiotics or preservatives from which to select are well known to the skilled artisan.

Methods of Vaccine Administration

The compositions described herein are suitable for induction of immune response against Spike protein of a coronavirus. The compositions described herein are also suitable for the use as a vaccine, i.e., the administration of the immunogenic composition disclosed herein leads to the induction of protective immune response against the coronavirus and thus preventing a subject in need thereof from being infected with said coronavirus, or, if said subject still gets infected, for reduction of the number and/or severity of the symptoms of said coronavirus infection.

In certain embodiments, the subject in need of the vaccination is a bovine, an ovine, a porcine, an equine, or an avian (e.g., chicken, turkey, geese or ducks) subject. In certain embodiments the subject is a canine, a feline or an animal of Mustellidae family (including minks, ferrets, sables and weasels). In other embodiments, the subject is a simian or a human.

The immunogenic compositions according to the invention may be administered according to the following regimen: a prime dose followed by the boost (or booster) dose about 14 to about 42 days after the prime dose. In different embodiments, the booster dose is administered about 14 to about 28 days, or about 21 days after the prime dose. In certain embodiments, this regimen provides at least a six-month duration of immunity after the booster dose, and preferably, at least a 12-month duration of immunity (e.g., 6 month-long, 7 month-long, 8 month-long, 9 month-long, 10 month-long, 11 month-long duration of immunity). Thus, in certain embodiments, semi-annual or annual revaccinations are envisioned.

The immunogenic compositions according to the invention may be formulated for and be administered to the subject by any known routes, including the oral, intranasal, mucosal, topical, transdermal, and parenteral (e.g., intravenous, intraperitoneal, intradermal, subcutaneous or intramuscular). Administration can also be achieved using needle-free delivery devices. Administration can be achieved using a combination of routes, e.g., the prime administration using a parental route and the boost administration using a mucosal route.

The invention will now be described in the following non-limiting examples.

EXAMPLES

Example 1

The objective of the study is to evaluate the efficacy of a recombinant SARS-CoV-2 trimer spike protein vaccine in dogs via the generation of antibodies with the ability to neutralize SARS-CoV-2 in vitro. The vaccine protein is recognized as a target of antibody mediated binding. The protein is similar to that utilized for human SARS and MERS vaccines.

Six- to eleven-month-old male (castrated) and female beagle dogs were used in this study. Nine of these dogs had previous exposure to Canine Parvovirus (orally administered MLV vaccine and CPV2c challenge), Canine Parainfluenza Virus (orally administered MLV vaccine and CPIV challenge strain D008), and canine distemper virus (orally administered MLV vaccine). Six of these dogs had previous exposure to canine distemper virus (orally administered MLV vaccine). The dogs were healthy and negative to SARS-CoV-2 via PCR by oropharyngeal swabs prior to Day 0.

Animals were maintained in an appropriate housing environment to meet USDA Animal Welfare Regulations (9 Code of Federal Regulations, Chapter 1, Subchapter A—Animal Welfare), AAALAC (Association for Assessment and Accreditation of Laboratory Animal Care) and Institutional Animal Care and Use Committee (IACUC) guidelines. The dogs were fed dry food suitable for the age and nutritional requirements of the animals, moistened if necessary, and provided ad libitum at least once daily through the course of the study. Canned food or non-medicated nutritional supplements were given as needed. Water was available ad libitum at all times.

The dogs were randomly assigned to one of three groups, as provided in Table 1.

TABLE 1

| Trt Group | No. of Animals | Vaccination Details | Day | Dose | Route | Blood Collection | End of Study |
|---|---|---|---|---|---|---|---|
| T01 | 5 | REHYDRAGEL ® ONLY (Control) | 0, 21 | 1.0 mL | SubQ | 0, 21, 42 | 42 |
| T02 | 5 | 20 µg recombinant Trimer Spike protein (SEQ ID NO: 17) with 1% v/v REHYDRAGEL ® adjuvant, Q.S. with 0.063% PBS (LP), pH = 7.4 | | | | | |
| T03 | 5 | 20 µg recombinant Trimer Spike protein (SEQ ID NO: 17) with adjuvant containing Quil A - 20 µg; Cholesterol - 20 µg; SEQ ID NO: 8 - 20 µg per dose), Q.S. with 0.063% PBS (LP), pH = 7.4 | | | | | |

Blood for pre-screening (approximately 3.0-6.0 mL) was collected prior to Day 0 for titer screening. Blood was collected in SST tubes from all animals.

Blood samples (approximately 6.0-12.0 mL or as appropriate for individual dog weight and blood collection guidelines) for serology were collected in SST tubes from all animals on Days 0 and 21, either a day before vaccination (i.e., day −1 and day 20) or the day of the vaccination but before the vaccination itself. On Day 42 (the end of the study) the maximum blood volume was calculated for each animal based on individual animal weight and IACUC guidelines. Blood was collected in SST tubes from all animals.

All animals were observed once on Day −1, twice on Day 0 (prior to and 3-6 hours post-vaccination), once daily on Days 1-5, twice on Day 21 (prior to and 3-6 hours post-vaccination), once daily on Days 22-26. Clinical observations were for approximately 30 minutes per session.

Injection site observations were recorded on Study Days 0 (prior to vaccination and 3-6 hours after), 1 through 5 for the first injection site (left shoulder). Injection site observations were recorded on Study Days 21 (prior to vaccination and 3-6 hours after), 22 through 26 (right shoulder).

The vaccines were well-tolerated by the dogs. No injection site pain or swelling observed during the study. Mild elevations of tympanic temperatures were observed in all study groups post-both vaccinations. No abnormal clinical signs were observed in any animals.

For the measurement of SN titer, a known quantity of the virus was combined with different dilutions of inactivated sera from the test animals. SN titer was measured by assessing viability of Vero E6 cells after the cells were incubated with the mixture of the virus and different dilution of the sera. See Tan et al., *Nat Biotech* 38:1073-78 (September 2020) and Wang et al., *J Immunol. Methods* 301:21-30 (2005).

For the determination of ELISA titer, plates were coated with 100 μl/well of 250 ng/ml protein (SEQ ID NO: 13) in coating buffer.

Peroxidase conjugated rabbit anti-dog IgG (H+L), polyclonal antibody (Jackson ImmunoResearch #304-035-003, lot 135618) was used as a secondary antibody and TMB Microwell Peroxidase Substrate DAKO True Blue #1601 was used as the substrate. Sera were initially diluted 1:300 followed by 1:3 serial dilutions. Secondary antibody was diluted 1:30,000 in PBST (PBS+0.05% (w/v) TWEEN®-20). 100 μl/well of sample serum dilution was added to the plates, and the plates were incubated and incubated at room temperature for 60 minutes. Secondary antibody was diluted 1:30,000 in dilution buffer, and 100 μl/well of this solution was added to the wells, and the reaction proceeded for 30 minutes. The plates were washed (4× with PBST) after sample incubation and after incubation with the secondary antibody.

Lateral flow test is a semi-quantitative test. Generally, it is a binary test to determine whether the animal has or lacks antibodies to SARS-CoV2 by the presence or the absence of the visible band indicating the presence of the antibodies. However, but lateral flow device may also measure the intensity of the band thus providing a semi-quantitative measure of the amount of the antibodies. For convenience, this semi-quantitative measure is referred to as LF titer, or "titer measured by LF" or the like. It should be understood, however, that as applied to the Lateral Flow measurements, the term "titer" is not a titer, in the strict sense.

Lateral Flow titer was measured by loading the sample and a chase buffer containing a blocker protein such as BSA, a buffer to maintain pH, Tween 20, sodium azide, and polyethylene glycol (PEG) 8000 to the sample well of a lateral flow device in which they are absorbed by a pad. The sample and buffer are wicked via capillary action through a deposit of colloidal gold conjugated with SEQ ID NO: 13.

The recombinant Spike protein-colloidal gold conjugate was prepared by adding a saturating quantity of protein to the gold and incubated for 10 minutes, followed by the addition of a BSA blocker and a stabilizer buffer including BSA and sucrose.

The antibody-gold complex continues to migrate down the test strip until it crosses a line of deposited reagent (Protein A or G) to immobilize antibodies. The cross-linking of the antibody-gold complex to the reagent on this line results in an accumulation of colloidal gold on the line, and a visible red line is formed.

SN titers as well as lateral flow measurements and ELISA for individual animals are summarized in tables 2, 3, and 4, respectively.

TABLE 2

| Animal ID | Treatment Group | SN Day 0 | SN Day 21 | SN Day 42 |
|---|---|---|---|---|
| 6591558 | T01 | <32 | <32 | <32 |
| 6591183 | T01 | <32 | <32 | <32 |
| 6586457 | T01 | <32 | <32 | <32 |
| 6586384 | T01 | <32 | <32 | <32 |
| 6586279 | T01 | <32 | <32 | <32 |
| 6591094 | T02 | <32 | <64 | >2048 |
| 6590969 | T02 | <32 | 272 | >2048 |
| 6586490 | T02 | <32 | 55 | 563 |
| 6586341 | T02 | <32 | 536 | >2048 |
| 6586287 | T02 | <32 | <32 | 1026 |
| 6591540 | T03 | <32 | 489 | >2048 |
| 6591442 | T03 | <32 | 441 | >2048 |
| 6586422 | T03 | <32 | 258 | >2048 |
| 6586350 | T03 | <32 | 538 | >2048 |
| 6586295 | T03 | <32 | 160 | >2048 |

TABLE 3

| | | Day 0 | | Day 21 | | Day 42 | |
|---|---|---|---|---|---|---|---|
| Animal | Group | Visual | Titer | Visual | Titer | Visual | Titer |
| 6586279 | T01 | Neg | 4469 | Neg | 3411 | Neg | 5571 |
| 6586384 | T01 | Neg | 7147 | Neg | 11932 | Neg | 4243 |
| 6586457 | T01 | Neg | 3598 | Neg | 6952 | Neg | 5706 |
| 6591183 | T01 | Neg | 5632 | Neg | 10458 | Neg | 6727 |
| 6591558 | T01 | Neg | 3873 | Neg | 4010 | Neg | 7843 |
| 6586287 | T02 | Neg | 2420 | Pos | 20082 | Pos | 850922 |
| 6586341 | T02 | Neg | 7025 | Pos | 365099 | Pos | 908487 |
| 6586490 | T02 | Neg | 5456 | Pos | 295387 | Pos | 749547 |
| 6590969 | T02 | Neg | 5731 | Pos | 650084 | Pos | 964848 |
| 6591094 | T02 | Neg | 3604 | Pos | 132687 | Pos | 775755 |
| 6586295 | T03 | Neg | 3230 | Pos | 558603 | Pos | 757122 |
| 6586350 | T03 | Neg | 2552 | Pos | 695001 | Pos | 935679 |
| 6586422 | T03 | Neg | 3661 | Pos | 556414 | Pos | 985040 |
| 6591442 | T03 | Neg | 8359 | Pos | 541499 | Pos | 727335 |
| 6591540 | T03 | Neg | 3632 | Pos | 755504 | Pos | 793830 |

| Animal | Group | Titer Day 127 | Titer Day 155 | Titer Day 187 |
|---|---|---|---|---|
| 6586279 | T01 | 2,763 | 4,684 | 6,038 |
| 6586384 | T01 | 8,636 | 8,043 | 2,793 |
| 6586457 | T01 | 9,804 | 5,889 | 6,162 |
| 6591183 | T01 | 4,145 | 10,615 | 7,083 |
| 6591558 | T01 | 5,717 | 7,436 | 3,506 |
| 6586287 | T02 | 115,359 | 95,210 | 82,828 |
| 6586341 | T02 | 353,214 | 264,908 | 257,688 |
| 6586490 | T02 | 134,871 | 81,540 | 23,998 |
| 6590969 | T02 | 395,128 | 187,301 | 144,476 |
| 6591094 | T02 | 254,027 | 142,923 | 144,150 |
| 6586295 | T03 | 467,165 | 475,987 | 474,329 |
| 6586350 | T03 | 361,288 | 419,237 | 548,015 |
| 6586422 | T03 | 363,699 | 424,946 | 649,238 |
| 6591442 | T03 | 351,571 | 405,438 | 446,510 |
| 6591540 | T03 | 463,024 | 437,149 | 495,005 |

All animals from group T01 were negative and all animals from groups T02 and T03 were positive on days 127, 155, and 187 by visual observation.

TABLE 4

| Animal | Group | ELISA Day 0 | ELISA Day 21 | ELISA Day 42 | ELISA Day 99 | ELISA Day 127 | ELISA Day 155 | ELISA Day 187 |
| --- | --- | --- | --- | --- | --- | --- | --- | --- |
| 6586279 | T01 | 300 | 100 | <1000 | <300 | <300 | 300 | 300 |
| 6586384 | T01 | 100 | 100 | <1000 | 300 | 300 | 300 | 300 |
| 6586457 | T01 | 100 | 100 | <1000 | <300 | <300 | <300 | 300 |
| 6591183 | T01 | 100 | 100 | <1000 | 300 | 300 | 300 | 300 |
| 6591558 | T01 | 100 | 100 | <1000 | <300 | <300 | 300 | 300 |
| 6586287 | T02 | 300 | 8100 | 81000 | 8,100 | 2,700 | 900 | 900 |
| 6586341 | T02 | 100 | 8100 | 27000 | 24,300 | 8,100 | 2,700 | 2,700 |
| 6586490 | T02 | 100 | 8100 | 27000 | 24,300 | 2,700 | 900 | 900 |
| 6590969 | T02 | 100 | 2700 | 81000 | 24,300 | 8,100 | 900 | 900 |
| 6591094 | T02 | 100 | 8100 | 27000 | 8,100 | 2,700 | 900 | 900 |
| 6586295 | T03 | 100 | 8100 | 243000 | 24,300 | 24,300 | 8,100 | 8,100 |
| 6586350 | T03 | 100 | 8100 | 81000 | 24,300 | 24,300 | 8,100 | 8,100 |
| 6586422 | T03 | 100 | 8100 | 243000 | 24,300 | 8,100 | 8,100 | 8,100 |
| 6591442 | T03 | 100 | 8100 | 243000 | 72,900 | 8,100 | 8,100 | 8,100 |
| 6591540 | T03 | 100 | 24300 | 243000 | 24,300 | 8,100 | 8,100 | 8,100 |

No control animals seroconverted, as expected. In contrast each of the animals in group T02 and T03 seroconverted. All animals in groups T02 and T03 had protective titer on day 42.

Example 2

The objective of the study is to evaluate the efficacy of a recombinant SARS-CoV-2 trimer spike protein vaccine in cats via the generation of antibodies with the ability to neutralize SARS-CoV-2 in vitro.

Healthy domestic short hair cats of approximately ten months of age were used in the study. The cats were acclimatized for at least 14 days prior to use in the study.

All animals in the study were healthy prior to Day 0. All animals in the study were negative to SARS-CoV-2 by PCR via nasal swab and serology prior to Day 0. The animals were maintained in an appropriate housing environment to meet USDA Animal Welfare Regulations. Environmental conditions and floor space were consistent with the standard practices of the testing facility. The animas were fed with a diet according to their age requirement and provided with water ad libitum.

The randomization was produced using a SAS (SAS release 9.4 or higher, SAS Institute, Cary, NC) program developed specifically for the study with the ranuni function used to generate random numbers.

The animals were treated as summarized in Table 5 below.

TABLE 5

| Trt Group | No. of Animals | Vaccination Details | Day | Dose | Route | Blood Collection | End of Study |
|---|---|---|---|---|---|---|---|
| T01 | 5 | Control: Adjuvant only, as in T02 | 0, 21 | 1.0 mL | SubQ | 0, 21, 42 | 42 |
| T02 | 5 | Per dose: 20 μg recombinant Trimer Spike protein (SEQ ID NO: 17) adjuvant containing 20 μg Quil A, 20 μg Cholesterol, 10 μg DDA, 0.05% v/v CARBOPOL ®, Q.S. with DMEM PBS, pH = 7.5 | | | | | |
| T03 | 5 | Per dose: 20 μg recombinant Trimer Spike protein (SEQ ID NO: 17) with adjuvant containing 250 μg BAY1005 ® acetate, 50 μg SEQ ID NO: 8, Q.S. with DMEM PBS, pH = 6.8) | | | | | |

The animals were observed, and tympanic temperature was measured twice daily on day 0 (prior to and 3-6 hours post-vaccination), once daily on days −1, 1-5, twice on day 21 (prior to and 3-6 hours after the vaccination, once daily on days 22-26. Clinical observations were for approximately 30 minutes per session.

Injection site reactions were observed daily for 5 days after each vaccination (days 1-5 and 22-26) or until the reactions were no longer visible for call cats.

The vaccines were well-tolerated. No injection site pain or swelling were observed while on study. No abnormal clinical observations or elevated temperatures were observed while on study.

Antibody responses to the vaccination were measure by the measurement of serum neutralizing titer, by lateral flow assay and by ELISA.

SN titers and LF titers were measured as described in Example 1.

ELISA Titers were measured as described in Example 1 except in this study, the starting dilution was 1:100 (rather than 1:300) and the secondary antibody was diluted 1:40,000 rather than 1:30,000. The results for the individual animals are provided in tables 6 (SN titer), 7 (Lateral Flow), and 8 (ELISA).

TABLE 6

| Animal | Group | SN, Day 0 | SN Day 21 | SN Day 42 |
|---|---|---|---|---|
| M191610 | T01 | <32 | <32 | <32 |
| M191687 | T01 | <32 | <32 | <32 |
| M191814 | T01 | <32 | <32 | <32 |
| M191962 | T01 | <32 | <32 | <64 |
| M192021 | T01 | <32 | <32 | <32 |
| M191628 | T02 | <32 | <32 | >2048 |
| M191644 | T02 | <32 | <32 | >2048 |
| M191733 | T02 | <32 | >2048 | >2048 |
| M191776 | T02 | <32 | >2048 | >2048 |
| M191989 | T02 | <32 | 1371 | >2048 |
| M191725 | T03 | <32 | 558 | >2048 |
| M191857 | T03 | <32 | >2048 | >2048 |
| M191920 | T03 | <32 | 361 | >2048 |
| M192004 | T03 | <32 | 550.5 | >2048 |
| M191602 | T03 | <32 | >2048 | >2048 |

TABLE 7

| Animal | Group | Day 0 Visual | Day 0 Titer | Day 21 Visual | Day 21 Titer | Day 42 Visual | Day 42 Titer | Day 181 Titer | Day 265 Titer |
|---|---|---|---|---|---|---|---|---|---|
| M191610 | T01 | Neg | 8973 | Neg | 9288 | Neg | 10309 | 18580 | N/A |
| M191687 | T01 | Neg | 9545 | Neg | 10443 | Neg | 11800 | 16804 | N/A |
| M191814 | T01 | Neg | 9169 | Neg | 5292 | Neg | 7804 | 13916 | N/A |
| M191962 | T01 | Neg | 11614 | Neg | 7924 | Neg | 17164 | 9359 | N/A |
| M192021 | T01 | Neg | 5862 | Neg | 14558 | Neg | 12855 | 19127 | N/A |
| M191628 | T02 | Neg | 7526 | Pos | 188166 | Pos | 521160 | 171951 | 128861 |
| M191644 | T02 | Neg | 10431 | Pos | 293915 | Pos | 342056 | 245437 | 171481 |
| M191733 | T02 | Neg | 10775 | Pos | 221439 | Pos | 401849 | 186440 | 179934 |
| M191776 | T02 | Neg | 14205 | Pos | 247635 | Pos | 462343 | 314616 | 288543 |
| M191989 | T02 | Neg | 5853 | Pos | 226459 | Pos | 411664 | 267826 | 208967 |
| M191725 | T03 | Neg | 9878 | Pos | 142507 | Pos | 375131 | 534069 | 626340 |
| M191857 | T03 | Neg | 14056 | Pos | 243948 | Pos | 252345 | 287385 | 304955 |
| M191920 | T03 | Neg | 6730 | Pos | 164120 | Pos | 438883 | 412096 | 440451 |
| M192004 | T03 | Neg | 11400 | Pos | 157025 | Pos | 540735 | 437773 | 494968 |
| M191602 | T03 | Neg | 7066 | Pos | 20709 | Pos | 363478 | 398709 | 623569 |

| Animal | Group | Day 419 Visual | Day 419 Titer |
|---|---|---|---|
| M191610 | T01 | N/A | N/A |
| M191687 | T01 | N/A | N/A |
| M191814 | T01 | N/A | N/A |
| M191962 | T01 | N/A | N/A |
| M192021 | T01 | N/A | N/A |
| M191628 | T02 | Pos | 72,433 |
| M191644 | T02 | Pos | 73,167 |
| M191733 | T02 | Pos | 138,427 |
| M191776 | T02 | Pos | 149,226 |
| M191989 | T02 | Pos | 159,924 |
| M191725 | T03 | Pos | 263,788 |
| M191857 | T03 | Pos | 374,334 |
| M191920 | T03 | Pos | 153,351 |
| M192004 | T03 | Pos | 188,604 |
| M191602 | T03 | Pos | 383,614 |

N/A - Sample not analyzed

All animals from group T01 were negative and all animals from groups T02 and T03 were positive on days 181 and 265 by visual observation.

TABLE 8

| Animal | Group | ELISA Day 0 | ELISA Day 21 | ELISA Day 42 | ELISA Day 86 | ELISA Day 115 | ELISA Day 148 | ELISA Day 181 | ELISA Day 265 |
|---|---|---|---|---|---|---|---|---|---|
| M191610 | T01 | 900 | 300 | 300 | 300 | 900 | 900 | 900 | N/A |
| M191687 | T01 | 100 | 100 | 100 | <300 | <300 | <300 | <300 | N/A |
| M191814 | T01 | 900 | 300 | 300 | 300 | 900 | 300 | 300 | N/A |
| M191962 | T01 | 300 | 300 | 300 | 300 | 300 | <300 | 300 | N/A |
| M192021 | T01 | 100 | 100 | 100 | <300 | 300 | <300 | <300 | N/A |

TABLE 8-continued

| | | | | | | | | |
|---|---|---|---|---|---|---|---|---|
| M191628 | T02 | 300 | 24300 | 72900 | 72900 | 72900 | 72900 | 72900 | 24300 |
| M191644 | T02 | 300 | 24300 | 72900 | 72900 | 24300 | 24300 | 24300 | 24300 |
| M191733 | T02 | 900 | 72900 | 72900 | 72900 | 24300 | 24300 | 24300 | 24300 |
| M191776 | T02 | 100 | 24300 | 72900 | 72900 | 24300 | 24300 | 24300 | 24300 |
| M191989 | T02 | 300 | 24300 | 72900 | 72900 | 72900 | 72900 | 24300 | 24300 |
| M191725 | T03 | 900 | 8100 | 72900 | 72900 | 72900 | 72900 | 72900 | 72900 |
| M191857 | T03 | 300 | 24300 | >218700 | 218700 | 72900 | 72900 | 72900 | 72900 |
| M191920 | T03 | 300 | 24300 | >218700 | 218700 | 72900 | 72900 | 72900 | 72900 |
| M192004 | T03 | 300 | 8100 | >218700 | 72900 | 72900 | 72900 | 72900 | 72900 |
| M191602 | T03 | 300 | 8100 | >218700 | 218700 | 72900 | 218700 | 72900 | 72900 |

| Animal | Group | ELISA D289 | ELISA D300 | ELISA D328 | ELISA D356 | ELISA D384 | ELISA D419 |
|---|---|---|---|---|---|---|---|
| M191610 | T01 | N/A | N/A | N/A | N/A | N/A | N/A |
| M191687 | T01 | N/A | N/A | N/A | N/A | N/A | N/A |
| M191814 | T01 | N/A | N/A | N/A | N/A | N/A | N/A |
| M191962 | T01 | N/A | N/A | N/A | N/A | N/A | N/A |
| M192021 | T01 | N/A | N/A | N/A | N/A | N/A | N/A |
| M191628 | T02 | 24,300 | 24,300 | 24,300 | 24,300 | 24,300 | 24,300 |
| M191644 | T02 | 24,300 | 24,300 | 24,300 | 8,100 | 8,100 | 8,100 |
| M191733 | T02 | 24,300 | 24,300 | 24,300 | 24,300 | 24,300 | 24,300 |
| M191776 | T02 | 24,300 | 24,300 | 8,100 | 8,100 | 8,100 | 24,300 |
| M191989 | T02 | 24,300 | 24,300 | 24,300 | 24,300 | 8,100 | 24,300 |
| M191725 | T03 | 72,900 | 72,900 | 72,900 | 72,900 | 72,900 | 72,900 |
| M191857 | T03 | 72,900 | 24,300 | 24,300 | 24,300 | 24,300 | 72,900 |
| M191920 | T03 | 72,900 | 72,900 | 72,900 | 72,900 | 72,900 | 72,900 |
| M192004 | T03 | 72,900 | 72,900 | 72,900 | 72,900 | 24,300 | 24,300 |
| M191602 | T03 | 72,900 | 72,900 | 72,900 | 72,900 | 72,900 | 72,900 |

N/A - Sample not analyzed

These data demonstrate that the vaccines according to the invention cause robust immune response against COVID-19 spike protein and that the immune response persists for at least 265 days or more, e.g., twelve months or more, or thirteen months or more, or 419 days.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

The invention claimed is:

1. A composition comprising a protein whose amino acid sequence consists of SEQ ID NO: 17, and an adjuvant consisting of a saponin, a sterol, and a CpG-containing immunostimulatory oligonucleotide.

2. The composition according to claim 1, wherein the Saponin is a triterpenoid saponin extracted from bark of *Quillaia Saponaria* and the sterol is selected from the group consisting of β-sitosterol, stigmasterol, ergosterol, ergocalciferol, and cholesterol.

3. The composition according to claim 2, wherein the saponin is present in the amount of about 20 μg per dose and the sterol is present in the amount of about 20 μg per dose.

4. The composition according to claim 1, wherein the immunostimulatory oligonucleotide is a P-class immunostimulatory oligonucleotide characterized by the presence of one or more TLR-9 activating motif(s) and two palindromes or two complementarity areas.

5. The composition according to claim 4 wherein said P-class immunostimulatory oligonucleotide is 5' modified.

6. The composition according to claim 5, wherein said P class immunostimulatory oligonucleotide comprises at least 22 contiguous nucleotides of SEQ ID NO: 8.

7. The composition according to claim 1, wherein the CpG containing immunostimulatory oligonucleotide is present in the amount of about 20 to about 50 μg per dose.

8. A method of inducing an immune response in a subject in need thereof, the method comprising administering to said subject the composition according to claim 1.

9. The method according to claim 8 wherein said subject is a canine.

10. The method according to claim 8 wherein said immunogenic composition is administered to said subject in a prime administration and in a boost administration, wherein the boost administration is between about 14 and about 42 days after the prime administration.

11. The method according to claim 8 wherein said immune response is a protective immune response.

12. The method according to claim 11 wherein said protective immune response is retained for at least six months after the boost administration.

13. The method according to claim 12 wherein said protective immune response is retained for at least 12 months after the boost administration.

* * * * *